United States Patent
Sullivan

(10) Patent No.: US 9,855,029 B2
(45) Date of Patent: *Jan. 2, 2018

(54) METHOD OF TISSUE REPAIR USING A TENSIONABLE KNOTLESS ANCHOR WITH SPLICE

(71) Applicant: Arthrex, Inc., Naples, FL (US)

(72) Inventor: Derek C. Sullivan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 351 days.

This patent is subject to a terminal disclaimer.

(21) Appl. No.: 14/698,533

(22) Filed: Apr. 28, 2015

(65) Prior Publication Data

US 2015/0245831 A1 Sep. 3, 2015

Related U.S. Application Data

(62) Division of application No. 13/615,986, filed on Sep. 14, 2012, now Pat. No. 9,107,653.

(Continued)

(51) Int. Cl.
*A61B 17/04* (2006.01)
*A61F 2/08* (2006.01)
*A61B 17/06* (2006.01)

(52) U.S. Cl.
CPC ...... *A61B 17/0401* (2013.01); *A61B 17/0466* (2013.01); *A61B 17/0485* (2013.01); *A61B 17/0487* (2013.01); *A61F 2/0811* (2013.01); *A61B 17/06166* (2013.01); *A61B 2017/0412* (2013.01); *A61B 2017/0414* (2013.01);

(Continued)

(58) Field of Classification Search
CPC . A61B 17/04; A61B 17/0401; A61B 17/0466; A61B 17/0487; A61B 17/0485; A61B 2017/06185; A61B 2017/0445; A61B 2017/0475; A61B 17/06166; A61B 2017/0458; A61B 2017/0496;

(Continued)

(56) References Cited

U.S. PATENT DOCUMENTS 330,087 A * 11/1885 Binns ................. A61B 17/0401
24/38
2,698,986 A * 1/1955 Brown .................... A01K 97/16
28/110

(Continued)

FOREIGN PATENT DOCUMENTS

DE 299 10 202 U1 9/1999
DE 201 01 791 U1 6/2001

(Continued)

*Primary Examiner* — Amy R Weisberg
(74) *Attorney, Agent, or Firm* — Blank Rome LLP

(57) ABSTRACT

A method of fixating soft tissue to bone using a bone anchor connected to a construct formed of a suture strand passing through the anchor and a shuttle device passing through a splice region of the suture strand. After installing the anchor in bone, an end of the suture strand is passed around or through soft tissue to be fixated, and then the end of the suture strand is inserted into an eyelet of the shuttling device. By pulling on the opposite end of the shuttling device, the end of the suture strand is passed through the splice region of the flexible strand, thereby forming a knotless closed loop having an adjustable perimeter. As the loop is tightened, the soft tissue is tensioned against the bone.

24 Claims, 22 Drawing Sheets

Related U.S. Application Data

(60) Provisional application No. 61/537,811, filed on Sep. 22, 2011, provisional application No. 61/663,024, filed on Jun. 22, 2012.

(52) U.S. Cl.
CPC ........... *A61B 2017/0445* (2013.01); *A61B 2017/0446* (2013.01); *A61B 2017/0458* (2013.01); *A61B 2017/0475* (2013.01); *A61B 2017/0496* (2013.01); *A61B 2017/06185* (2013.01); *A61F 2002/0852* (2013.01); *A61F 2002/0888* (2013.01)

(58) Field of Classification Search
CPC ........... A61B 2017/0446; A61F 2/0811; A61F 2002/0888; A61F 2002/0852
USPC ............... 606/232, 103, 113, 148, 300, 304
See application file for complete search history.

(56) References Cited

U.S. PATENT DOCUMENTS

| | | |
|---|---|---|
| 3,176,316 A | 4/1965 | Bodelll |
| 4,099,750 A * | 7/1978 | McGrew ............. D07B 1/185 114/221 R |
| 4,187,558 A | 2/1980 | Dahlen et al. |
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,062,344 A * | 11/1991 | Gerker .............. D07B 1/185 289/1.5 |
| 5,129,902 A | 7/1992 | Goble et al. |
| 5,156,616 A | 10/1992 | Meadows et al. |
| 5,171,274 A | 12/1992 | Fluckiger et al. |
| 5,211,647 A | 5/1993 | Schmieding |
| 5,217,495 A | 6/1993 | Kaplan et al. |
| 5,250,053 A * | 10/1993 | Snyder .............. A61B 17/0469 606/139 |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,517,542 A | 5/1996 | Huq |
| 5,534,011 A * | 7/1996 | Greene, Jr. ......... A61B 17/0485 606/232 |
| 5,562,669 A | 10/1996 | McGuire |
| 5,575,819 A | 11/1996 | Amis |
| 5,628,756 A | 5/1997 | Barker et al. |
| 5,643,266 A | 7/1997 | Li |
| 5,645,588 A | 7/1997 | Graf et al. |
| 5,690,676 A * | 11/1997 | DiPoto .............. A61B 17/0401 606/232 |
| 5,699,657 A * | 12/1997 | Paulson ............. B65H 69/06 28/142 |
| 5,931,869 A | 8/1999 | Boucher et al. |
| 5,961,520 A | 10/1999 | Beck et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 * | 2/2001 | Seedhom ............. A61F 2/08 623/13.11 |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom et al. |
| 6,517,542 B1 * | 2/2003 | Papay ............. A61B 17/0401 606/232 |
| 6,517,578 B2 | 2/2003 | Hein |
| 6,533,802 B2 | 3/2003 | Bojarski et al. |
| 6,592,609 B1 * | 7/2003 | Bonutti ............. A61B 17/0401 606/232 |
| 6,991,636 B2 * | 1/2006 | Rose ................. A61B 17/0401 606/139 |
| 7,097,654 B1 | 8/2006 | Freedland |
| 7,217,279 B2 * | 5/2007 | Reese ................ A61B 17/0401 606/232 |
| 7,261,716 B2 * | 8/2007 | Strobel .............. A61B 17/8615 606/232 |
| 7,306,417 B2 * | 12/2007 | Dorstewitz ........... B60P 7/0823 410/100 |
| 7,320,701 B2 * | 1/2008 | Haut ................ A61B 17/0401 606/232 |
| 7,494,506 B2 | 2/2009 | Brulez et al. |
| 7,601,165 B2 * | 10/2009 | Stone ................ A61B 17/0401 606/232 |
| 7,686,838 B2 | 3/2010 | Wolf et al. |
| 7,713,286 B2 * | 5/2010 | Singhatat ........... A61B 17/0401 606/232 |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,820 B2 * | 11/2010 | Stone ................ A61B 17/0401 606/232 |
| 7,828,855 B2 | 11/2010 | Ellis et al. |
| 7,875,052 B2 * | 1/2011 | Kawaura ............ A61B 17/0057 606/213 |
| 7,875,057 B2 | 1/2011 | Cook et al. |
| 7,905,903 B2 * | 3/2011 | Stone ................ A61B 17/0401 606/232 |
| 7,914,539 B2 | 3/2011 | Stone et al. |
| 7,938,847 B2 | 5/2011 | Fanton et al. |
| 8,029,536 B2 * | 10/2011 | Sorensen ........... A61B 17/0401 606/218 |
| 8,088,130 B2 | 1/2012 | Kaiser et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 8,277,484 B2 * | 10/2012 | Barbieri ............. A61B 17/0401 606/232 |
| 8,460,322 B2 * | 6/2013 | Van der Burg .... A61B 17/0401 606/144 |
| 8,460,340 B2 * | 6/2013 | Sojka ................ A61B 17/0401 606/230 |
| 8,500,809 B2 * | 8/2013 | Saliman ............. A61B 17/0401 623/13.11 |
| 8,652,171 B2 * | 2/2014 | Stone ................ A61B 17/0401 606/213 |
| 8,652,172 B2 * | 2/2014 | Denham ............ A61B 17/0401 606/228 |
| 8,758,406 B2 * | 6/2014 | Fanton ............... A61B 17/0401 606/232 |
| 8,771,315 B2 * | 7/2014 | Lunn ................. A61B 17/0401 606/232 |
| 8,814,905 B2 * | 8/2014 | Sengun .............. A61B 17/0401 289/1.5 |
| 8,821,543 B2 * | 9/2014 | Hernandez ......... A61B 17/0401 606/139 |
| 8,821,545 B2 | 9/2014 | Sengun |
| 8,932,331 B2 * | 1/2015 | Kaiser ................ A61B 17/0401 606/228 |
| 8,936,621 B2 * | 1/2015 | Denham ............ A61B 17/0401 606/228 |
| 2001/0041938 A1 | 11/2001 | Hein |
| 2002/0052629 A1 * | 5/2002 | Morgan .............. A61B 17/0401 606/232 |
| 2002/0161439 A1 | 10/2002 | Strobel et al. |
| 2003/0114929 A1 | 6/2003 | Knudsen et al. |

(56) References Cited

U.S. PATENT DOCUMENTS

| | | |
|---|---|---|
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0122608 A1* | 6/2006 | Fallin ............... A61B 17/0401 606/232 |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez et al. |
| 2007/0156148 A1* | 7/2007 | Fanton ............... A61B 17/0401 606/326 |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0185494 A1 | 8/2007 | Reese et al. |
| 2007/0203508 A1 | 8/2007 | White et al. |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0009904 A1* | 1/2008 | Bourque ............ A61B 17/0401 606/232 |
| 2008/0046009 A1 | 2/2008 | Albertorio et al. |
| 2008/0109037 A1* | 5/2008 | Steiner ............... A61B 17/0401 606/232 |
| 2008/0140092 A1* | 6/2008 | Stone ................ A61B 17/0401 606/144 |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0255613 A1* | 10/2008 | Kaiser ................ A61B 17/0401 606/232 |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0069847 A1* | 3/2009 | Hashiba ............. A61B 17/0487 606/232 |
| 2009/0082805 A1* | 3/2009 | Kaiser ................ A61B 17/0401 606/228 |
| 2009/0187244 A1 | 7/2009 | Dross |
| 2009/0192546 A1* | 7/2009 | Schmieding ....... A61B 17/0401 606/232 |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1* | 12/2009 | Kaiser ................ A61B 17/0401 606/148 |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0160962 A1* | 6/2010 | Dreyfuss .......... A61B 17/06166 606/228 |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292733 A1* | 11/2010 | Hendricksen ...... A61B 17/0401 606/232 |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0071545 A1 | 3/2011 | Pamichev et al. |
| 2011/0087283 A1* | 4/2011 | Donnelly ........... A61B 17/0401 606/232 |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1* | 8/2011 | Gadikota ........... A61B 17/686 623/13.14 |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053627 A1* | 3/2012 | Sojka ................ A61B 17/0401 606/232 |
| 2012/0053630 A1* | 3/2012 | Denham ............ A61B 17/0401 606/232 |
| 2012/0065732 A1 | 3/2012 | Roller et al. |
| 2012/0071896 A1* | 3/2012 | Ferree ............... A61B 17/0401 606/139 |
| 2012/0089143 A1 | 4/2012 | Martin et al. |
| 2012/0089193 A1* | 4/2012 | Stone ................ A61B 17/0401 606/301 |
| 2012/0109299 A1 | 5/2012 | Li et al. |
| 2012/0123473 A1* | 5/2012 | Hernandez ........ A61B 17/0401 606/232 |
| 2012/0123474 A1 | 5/2012 | Zajac et al. |
| 2012/0123541 A1* | 5/2012 | Albertorio ......... A61B 17/0401 623/13.14 |
| 2012/0130424 A1* | 5/2012 | Sengun ............. A61B 17/0401 606/232 |
| 2012/0150297 A1 | 6/2012 | Denham et al. |
| 2012/0158051 A1* | 6/2012 | Foerster ............ A61B 17/0401 606/232 |
| 2012/0165867 A1* | 6/2012 | Denham ............ A61B 17/0401 606/232 |
| 2012/0165938 A1 | 6/2012 | Denham et al. |
| 2012/0179199 A1* | 7/2012 | Hernandez ........ A61B 17/0401 606/232 |
| 2012/0197271 A1 | 8/2012 | Astorino et al. |
| 2012/0239085 A1* | 9/2012 | Schlotterback ....... A61B 17/04 606/228 |

(56) References Cited

U.S. PATENT DOCUMENTS

| | | | |
|---|---|---|---|
| 2012/0290003 A1* | 11/2012 | Dreyfuss | A61B 17/0401 606/232 |
| 2012/0296345 A1 | 11/2012 | Wack et al. | |
| 2012/0330357 A1* | 12/2012 | Thal | A61B 17/0401 606/232 |
| 2013/0023928 A1* | 1/2013 | Dreyfuss | A61B 17/0401 606/228 |
| 2013/0023929 A1 | 1/2013 | Sullivan et al. | |
| 2013/0072975 A1* | 3/2013 | Van Der Burg | A61B 17/0401 606/232 |
| 2013/0085528 A1* | 4/2013 | DiMatteo | A61B 17/0401 606/232 |
| 2013/0096612 A1* | 4/2013 | Zajac | A61B 17/0401 606/232 |
| 2013/0123842 A1* | 5/2013 | Chan | A61B 17/0401 606/232 |
| 2013/0131723 A1* | 5/2013 | Snell | A61B 17/0401 606/232 |
| 2013/0144338 A1* | 6/2013 | Stone | A61B 17/0401 606/232 |
| 2013/0190818 A1* | 7/2013 | Norton | A61B 17/0401 606/232 |
| 2013/0190819 A1* | 7/2013 | Norton | A61B 17/0401 606/232 |
| 2013/0345749 A1* | 12/2013 | Sullivan | A61B 17/0401 606/232 |
| 2013/0345750 A1* | 12/2013 | Sullivan | A61B 17/0401 606/232 |
| 2014/0039551 A1* | 2/2014 | Donahue | A61B 17/0401 606/232 |
| 2014/0052179 A1* | 2/2014 | Dreyfuss | A61B 17/0401 606/232 |
| 2014/0121700 A1 | 5/2014 | Dreyfuss et al. | |
| 2014/0142627 A1 | 5/2014 | Hendricksen et al. | |
| 2014/0257378 A1* | 9/2014 | Norton | A61B 17/06166 606/228 |
| 2014/0257382 A1* | 9/2014 | McCartney | A61B 17/0401 606/232 |
| 2014/0257384 A1* | 9/2014 | Dreyfuss | A61B 17/0401 606/232 |
| 2014/0276992 A1* | 9/2014 | Stone | A61B 17/0401 606/148 |
| 2015/0032157 A1* | 1/2015 | Dooney, Jr. | A61B 17/0401 606/232 |

FOREIGN PATENT DOCUMENTS

| | | |
|---|---|---|
| EP | 0 440 991 A1 | 8/1991 |
| EP | 1 108 401 A1 | 6/2001 |
| EP | 1 707 127 A1 | 10/2006 |
| WO | WO 03/022161 A1 | 3/2003 |
| WO | WO 2006/037131 A2 | 4/2006 |
| WO | WO 2007/002561 A1 | 1/2007 |
| WO | WO 2007/109769 A1 | 9/2007 |
| WO | WO 2008/091690 A1 | 7/2008 |

* cited by examiner

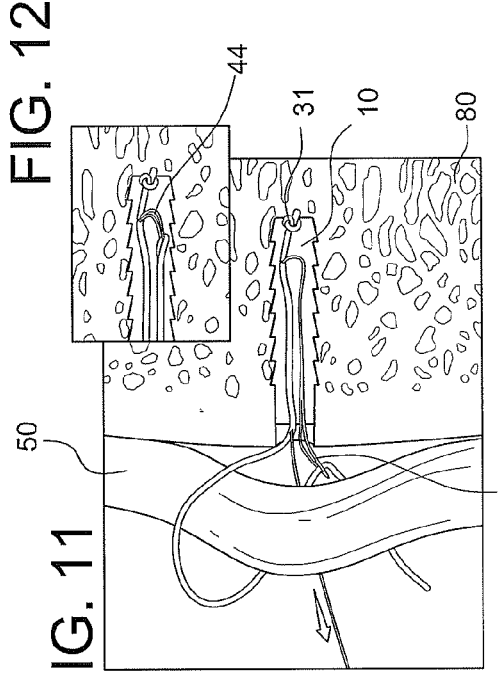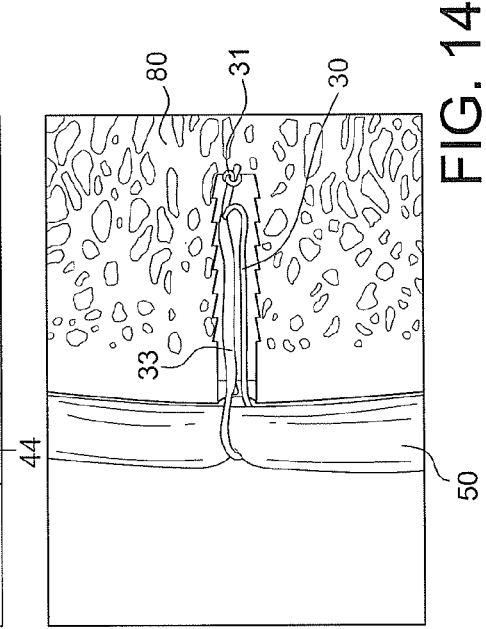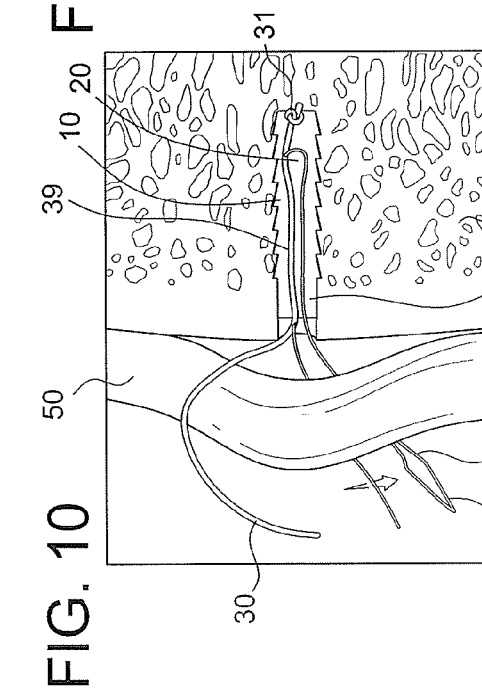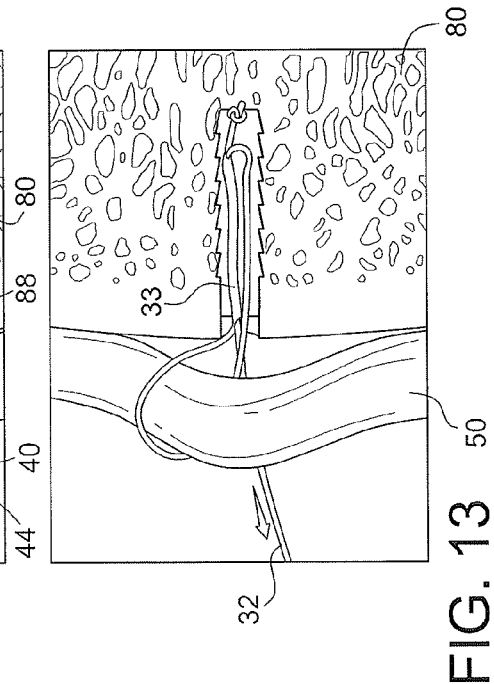

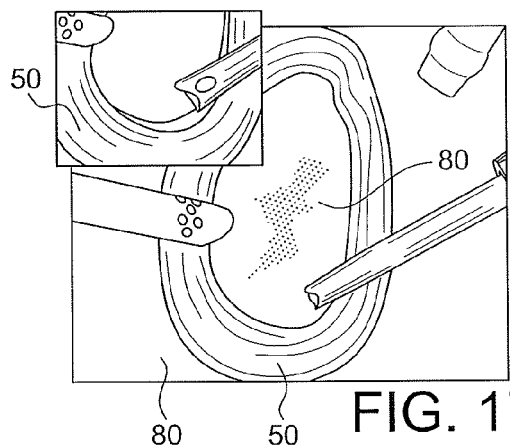
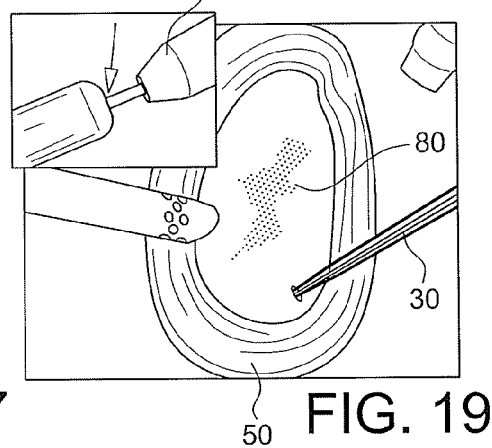
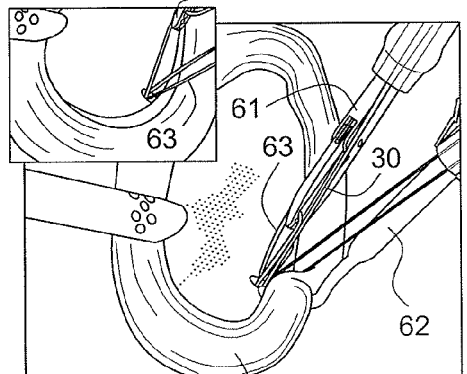
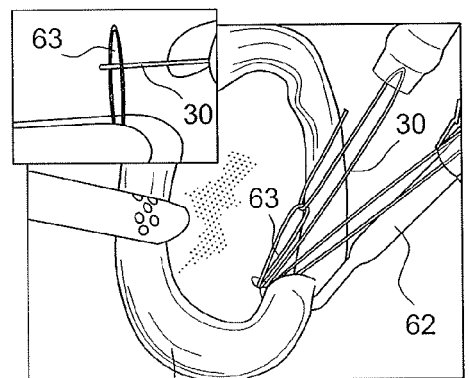

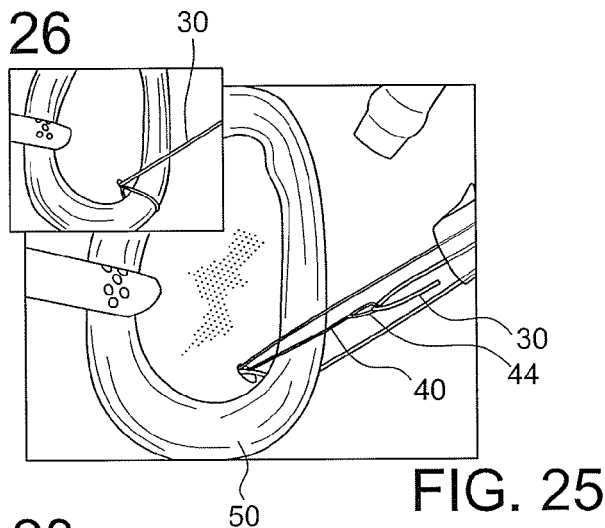
FIG. 26
FIG. 25
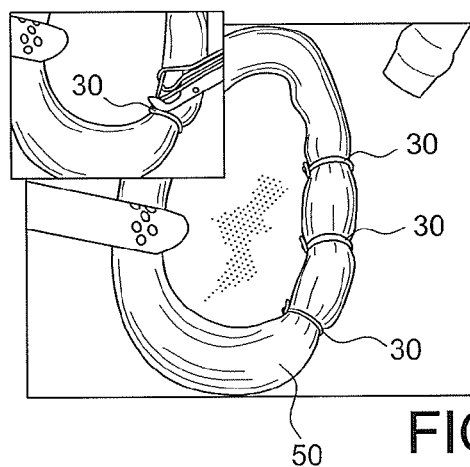
FIG. 28
FIG. 27
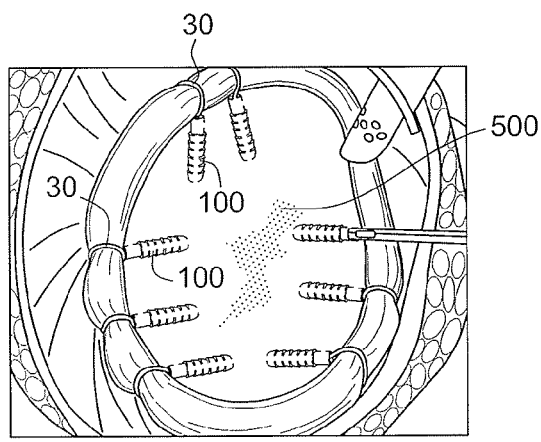
FIG. 29
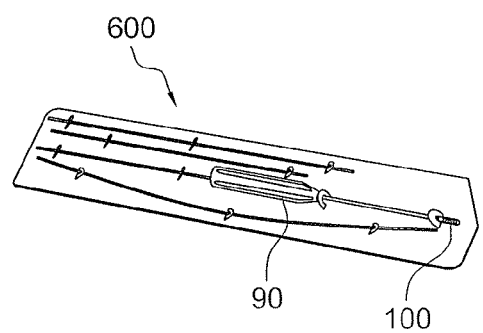
FIG. 30

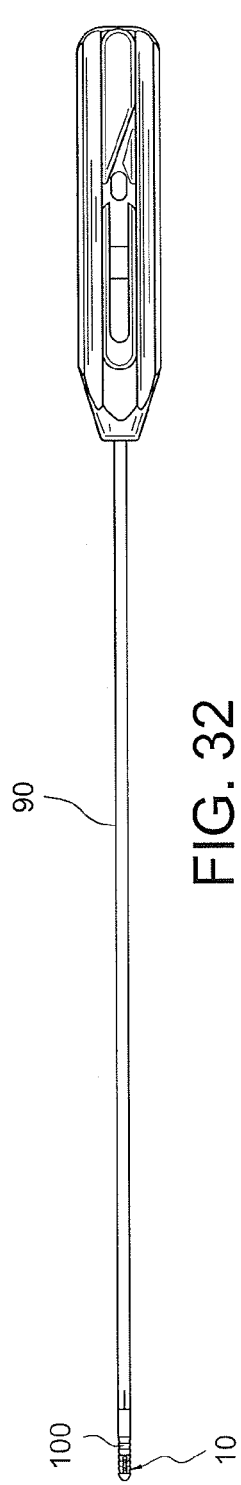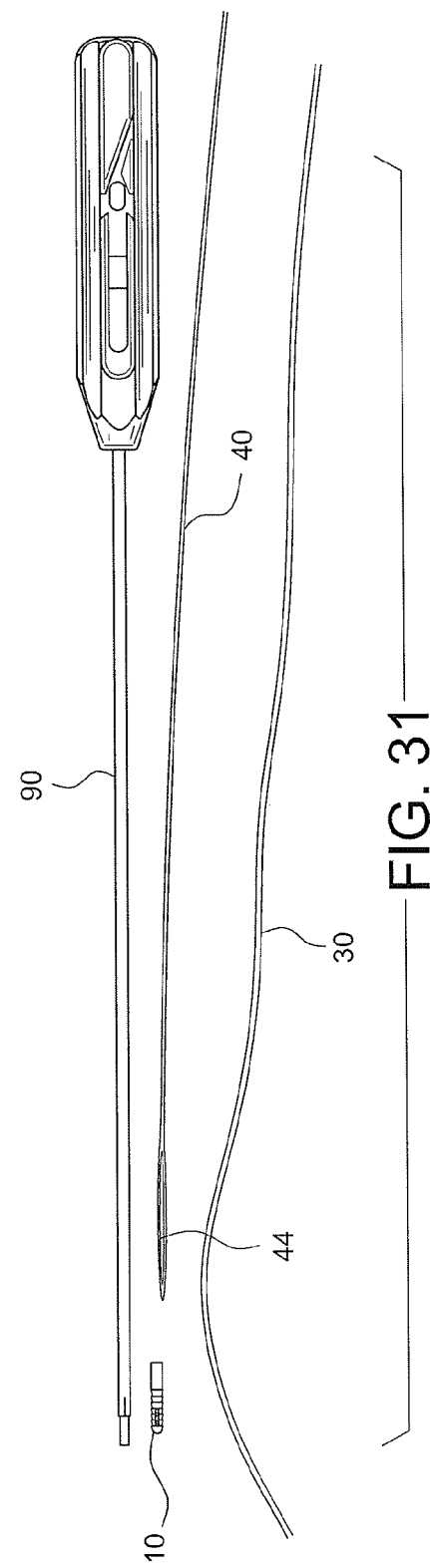

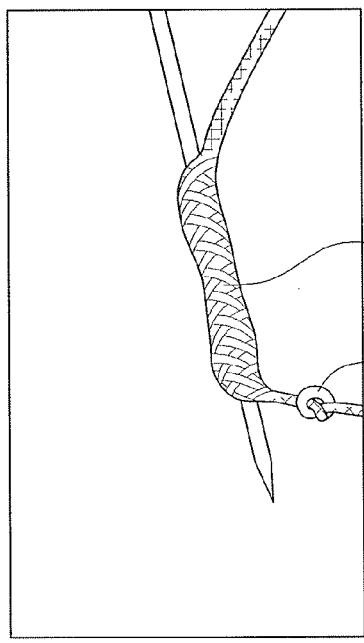
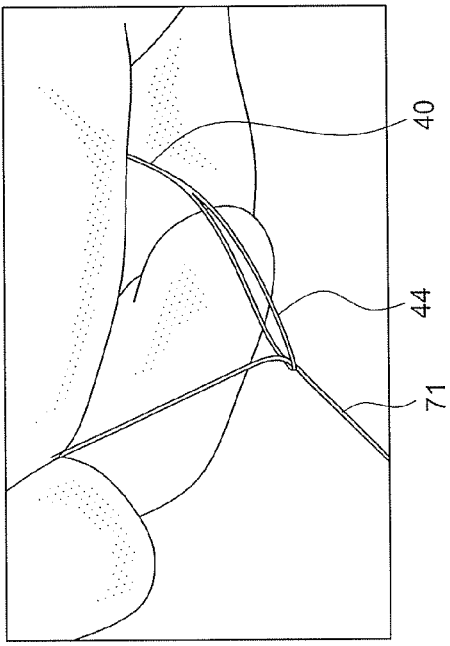
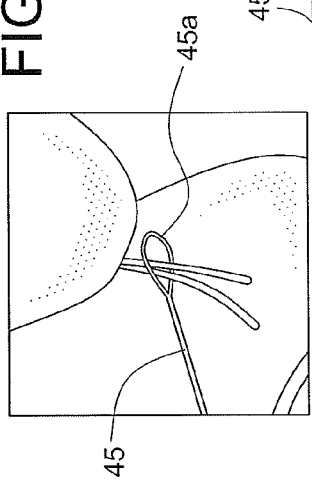
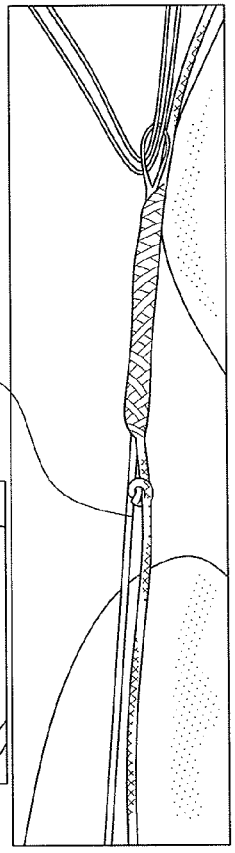
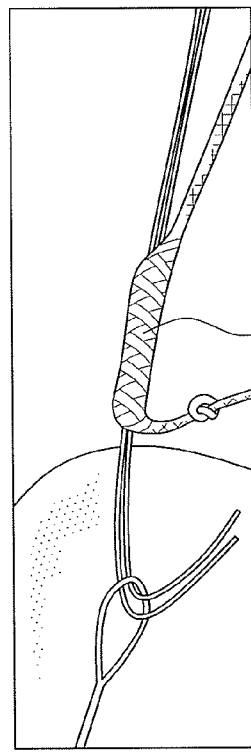

METHOD OF TISSUE REPAIR USING A TENSIONABLE KNOTLESS ANCHOR WITH SPLICE

CROSS-REFERENCE TO RELATED APPLICATIONS

This is a division of application Ser. No. 13/615,986, filed Sep. 14, 2012, which claims the benefit of U.S. Provisional Application No. 61/537,811, filed Sep. 22, 2011, and of U.S. Provisional Application No. 61/663,024, filed Jun. 22, 2012, the disclosures of both of which are incorporated by reference in their entirety herein.

FIELD OF THE INVENTION

The present invention relates to surgical devices and, in particular, to devices for repair or fixation of soft tissue to bone without the need for knots.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

There is a need for a knotless anchor which has a design that allows tensioning of the suture as necessary and after insertion into bone. Also needed is a tensionable anchor that does not require tying of knots and allows adjustment of both the tension of the suture and the location of the tissue with respect to the bone.

SUMMARY OF THE INVENTION

The present invention fulfills the above needs and objectives by providing a knotless, tensionable suture anchor. The suture anchor of the present invention has a configuration which allows the suture to be spliced and passed through itself within the suture anchor, to create a construct that is tensionable after insertion in bone (to allow attached tissue to be brought proximate to bone) and does not require tying of any knots.

Other features and advantages of the present invention will become apparent from the following description of the invention.

BRIEF DESCRIPTION OF THE DRAWINGS

FIGS. 10-14 illustrate subsequent steps of a method of knotless SutureTak™ self-locking technology according to a method of the present invention (and with the surgical construct of FIGS. 2-5).

FIGS. 17-30 illustrate subsequent steps of an exemplary method of tissue repair (rotator cuff repair) with a surgical construct of the present invention.

FIGS. 31-72 illustrate subsequent steps of a method of assembling a surgical construct of the present invention (with a tensionable knotless anchor (knotless SutureTak), suture and suture passing device attached to the suture).

DETAILED DESCRIPTION OF THE EMBODIMENTS

Figure 1:
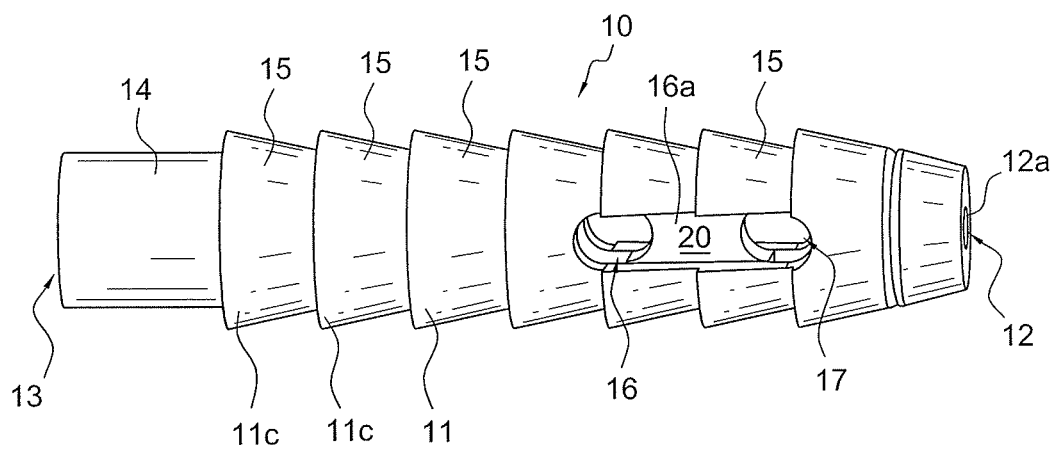
FIG. 1 illustrates a tensionable knotless anchor according to an exemplary embodiment of the present invention.

The present invention provides surgical constructs, systems and techniques for knotless soft tissue repair and fixation, such as fixation of soft tissue (ligament, tendon, graft, etc.) to bone. The surgical constructs comprise fixation devices (tensionable knotless anchors) that are inserted into bone with a suture mechanism (tensionable construct) formed of a flexible strand (a suture) provided within the fixation device and a shuttle/pull device (a suture passing instrument) attached to the flexible strand. The flexible strand and the shuttle/pull device attached to it allow formation of a splice within or outside the body of the anchor and during the tissue repair procedure (to finalize the construct). The shuttle/pull device is provided within the strand (inside of the strand) and forms the splice subsequent to the insertion of the fixation device within the bone (and subsequent to attachment to soft tissue to be repaired or fixated) to allow formation of the final fixation device with a knotless self-locking mechanism that allows the user (for example, the surgeon) to control the tension of the strand on the soft tissue to be attached to bone.

At least one of the flexible strand and the shuttle/pull device may be made of any known suture material, such as ultrahigh molecular weight poly ethylene (UHMWPE) or the FiberWire® suture (disclosed in U.S. Pat. No. 6,716,234 which is hereby incorporated by reference in its entirety). Typically the suture will be UHWMPE suture without a core to permit ease of splicing. The shuttle/pull device may be a shuttle/pull suture device such as a FiberLink™ or a Nitinol loop.

The present invention also provides methods of soft tissue repair which do not require tying of knots and allow adjustment of both the tension of the suture and the location of the tissue with respect to the bone. An exemplary method of the present invention comprises inter alia the steps of: (i) providing a surgical construct comprising a fixation device (for example, an anchor) with a flexible strand (for example, suture) and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice; and (v) pulling on the flexible strand to allow the soft tissue to achieve the desired location relative to the bone, and to allow proper tensioning of the final construct.

The flexible strand may be passed through at least a portion of the body of the fixation device (for example, through a full cannulation of the fixation device, or through a transversal opening at a distal end of the fixation device). Alternatively, the flexible strand may be fixed to the fixation device (which may be solid or cannulated) by overmolding the suture to the anchor body or by compressing the suture against the bone (achieving an interference fit between the fixation device and the bone tunnel, compressing the flexible strand). The splice may be formed within the body of the fixation device or outside the body of the fixation device. Upon insertion into the bone and tensioning, the splice may reside within the body of the fixation device or outside the body of the fixation device (but within a bone tunnel).

Another exemplary method of the present invention comprises inter alia the steps of: (i) providing a surgical construct comprising a fixation device (for example, an anchor) with a flexible strand (for example, suture) extending through the body of the fixation device and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice within the body of the fixation device (with the flexible strand passing through itself); and (v) pulling on the flexible strand to allow the soft tissue to achieve the desired location relative to the bone, and to allow proper tensioning of the final construct.

According to another exemplary method of the present invention, a method of tissue repair comprises inter alia the steps of: (i) providing a surgical construct comprising a fixation device (for example, an anchor) with a flexible strand (for example, suture) fixed to the fixation device and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice outside the body of the fixation device (i.e., with the flexible strand passing through itself and the splice being located outside the body of the fixation device); and (v) pulling on the flexible strand to allow the soft tissue to achieve the desired location relative to the bone, and to allow proper tensioning of the final construct.

Figure 3:
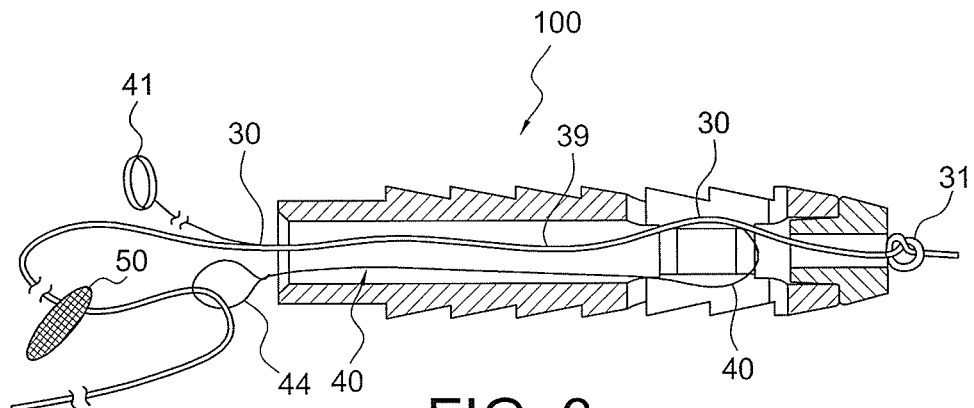
FIG. 3 illustrates the surgical construct of FIG. 2 with the suture threaded through the suture passing device.
Figure 4:
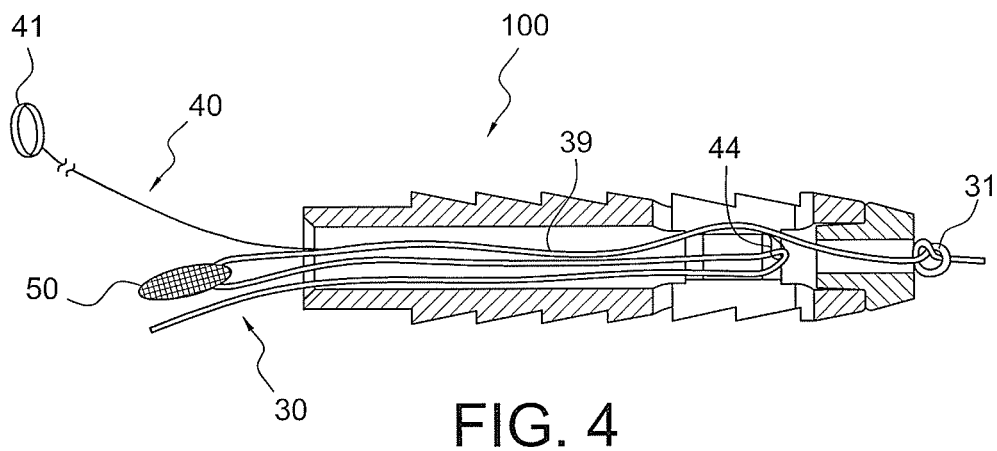
FIG. 4 illustrates the surgical construct of FIG. 3 during tensioning, wherein the suture has been pulled so that the suture passes through itself.
Figure 5:
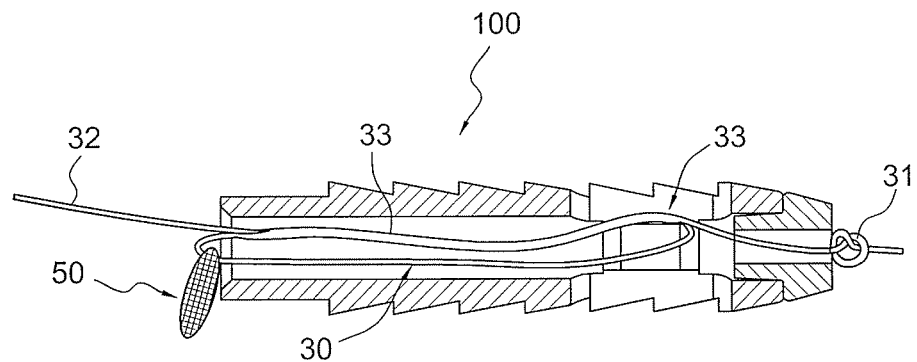
FIG. 5 illustrates the surgical construct of FIG. 4 after tensioning, wherein the suture has been pulled through itself to create a splice and the tissue has been pulled towards the bone.
Figure 8:
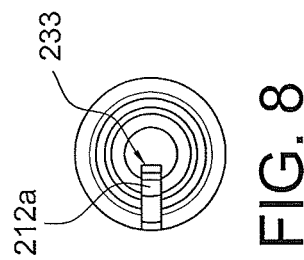
FIG. 8 is a right side view of the tensionable knotless anchor of FIG. 6.

Referring now to the drawings, where like elements are designated by like reference numerals, FIGS. 1-5 illustrate an exemplary fixation device 10 of the present invention employed to assemble surgical construct 100 (FIG. 5). In the particular exemplary embodiment illustrated in FIG. 1, fixation device 10 is a tensionable knotless anchor having an anchor body 11 provided with a longitudinal axis 11a, a proximal end 13 and a distal end 12, and a plurality of ribs 15 extending circumferentially around it. Openings/channels 16 and 17 allow threading suture(s) and/or suture passing device(s) to pass around post 20, as detailed below. Cannulation 11b extends along the body 11 to allow passage of flexible strands and of suture passing devices, as detailed below.

Cylindrical portion 14 is provided at the proximal end 13 of the anchor 10 and contains a socket 19 (FIG. 2) configured to securely engage a tip of a driver.

Openings/channels 16, 17 are positioned opposite to each other relative to the post 20 and also symmetrically located relative to the post 20, to allow flexible strand 30 (suture 30) and shuttle/pull device 40 (suture passing instrument 40) to pass and slide therethrough, as also detailed below. Openings/channels 16, 17 extend in a direction about perpendicular to the longitudinal axis 11a, and communicate through recesses 16a, 17a with the outer surfaces 11c of anchor body 11. Only recess 16a is shown in FIG. 1 (recess 17a is located on the opposite side of the recess 16a, i.e., on the anchor side facing away from the page). The position and size of the openings/channels 16, 17 and recesses 16a, 17a may be determined according to the characteristics of the flexible strand 30 and shuttle/pull device 40, and of the arthroscopic procedure, and the need to precisely orientate the anchor during insertion to optimize suture sliding characteristics.

Anchor 10 may be a screw-in anchor or a push-in style anchor. Anchor 10 may be formed of metal, biocompatible plastic such as PEEK or a bioabsorbable PLLA material. Socket 19 at the distal end 13 of the anchor 10 is configured to securely engage a tip of a driver, as detailed below. The socket of the anchor 10 may have any shape adapted to receive a driver tip for pushing tap-in or screw-in style anchors. Tensionable knotless anchor 10 may be made of one or more pieces, or may be provided as an integrated device.

Reference is now made to FIGS. 2-5 which illustrate the anchor 10 of FIG. 1 assembled with construct 99 (tensionable construct 99) formed of flexible strand or flexible material 30 (suture 30 or tie down suture 30) and shuttle/pull device 40 (suture passing instrument such as FiberLink™ 40 or a nitinol loop 40) attached to the flexible strand 30. In particular and exemplary-only embodiments, the flexible strand 30 is a suture strand 30 and the shuttle/pull device 40 is a suture passing device 40. Surgical construct 100 (FIG. 2) comprises tensionable knotless anchor 10 provided with flexible strand 30 passing through the body of the tensionable knotless anchor 10 and with shuttle/pull device 40 attached to the flexible strand 30. Details on assembling the construct 100 of the present invention (i.e., integrated system, surgical construct or surgical system 100 consisting of anchor 10, suture 30 and suture passing device 40 attached to the suture 30) are set forth below with reference to FIGS. 31-72.

Suture 30, which is typically braided or multi-filament, is preloaded onto the anchor by tying static knot 31, which prevents suture 30 from passing through distal blind hole 12a. The suture may also be preloaded by insert molding or by any other means known in the art. Suture 30 passes around post 20, which is large enough to allow suture 30 to take gradual turns instead of sharp turns. Suture 30 then passes through cannulation 11b and proximal blind hole 13a. Tensionable knotless anchor 10 is loaded onto a driver (not shown in FIGS. 1-5), and suture 30 is tied to the driver (for example, wrapped around a cleft of the driver) to fasten tensionable knotless anchor 10 securely to the driver.

Figure 2:
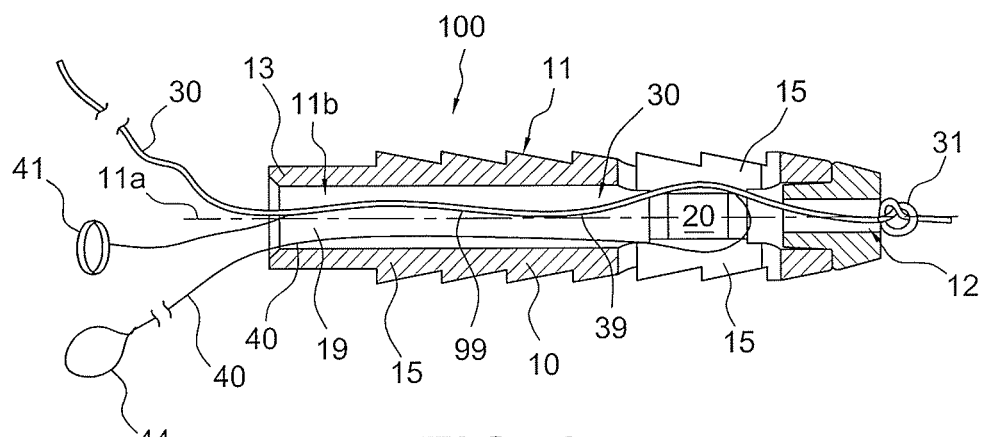
FIG. 2 is a cross-sectional view of a surgical construct according to an exemplary embodiment of the present invention (with the tensionable knotless anchor of FIG. 1, a suture and a suture passing device attached to the suture, before tensioning of the suture).

Prior to the fastening of the anchor 10 to the driver, suture passing device 40 (for example, a FiberLink™ or a nitinol loop) is threaded through suture 30 (i.e., attached to the suture 30 through splice region 39), as shown in FIG. 2. Suture passing device 40 includes an eyelet/loop 44 for passing suture and, optionally, a pull-ring 41. Suture passing device 40 passes through an aperture of suture 30, located either proximal or distal to distal blind hole 12a. It then exits an aperture of suture 30, within the tensionable knotless anchor 10, traverses around post 20, and through proximal blind hole 13a. Tensionable knotless anchor 10 loaded with tensionable construct 99 (formed of suture 30 attached to the suture passing device 40) is then secured into bone (for example, into a hole/socket/tunnel formed in the bone) by using the driver.

FIG. 3 depicts the tensionable knotless anchor 10 after it has been inserted into a drilled hole in bone, the suture released from the driver, and the driver removed. Suture 30 is then passed through (or around) the tissue 50 which is to be reattached to bone. Suture 30 is subsequently passed through eyelet/loop 44 of the suture passing device 40. Suture passing device 40 is then pulled by ring 41, thereby pulling suture 30 towards tensionable knotless anchor 10.

In FIG. 4, suture 30 has been further pulled towards tensionable knotless anchor 10 so that it doubles on itself inside tensionable knotless anchor 10. The suture passing device 40 has also been further pulled through the splice region of suture 30.

FIG. 5 illustrates surgical construct 100 with suture 30 after it has been pulled through itself, creating splice 33. Thus, the suture passing device (not visible) helps create splice 33 within tensionable knotless anchor 10 by facilitating suture 30 passing through itself. Once the suture 30 has been fully passed through itself, suture end 32 may be pulled until tissue 50 has been moved to the desired location, such as near a drilled hole in the bone. Once the desired tension and location is achieved, suture end 32 may be clipped off to complete the soft tissue repair or fixation.

The surgical construct 100 with the knotless anchor 10 and tensionable construct 99 of the invention offers the following advantages:

the tension and/or location of the tissue may be altered after the tensionable knotless anchor is implanted;

no knots need to be tied in the suture during the repair or fixation procedure, which makes the procedure faster, easier, and less costly;

there is no need to load the suture outside of the tensionable knotless anchor;

the suture may be loaded or pre-loaded on the inside of the tensionable knotless anchor; and no additional fasteners need to be used.

Figure 9:
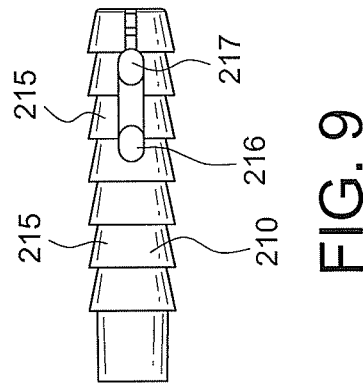
FIG. 9 is another side view of the tensionable knotless anchor of FIG. 6.
Figure 6:
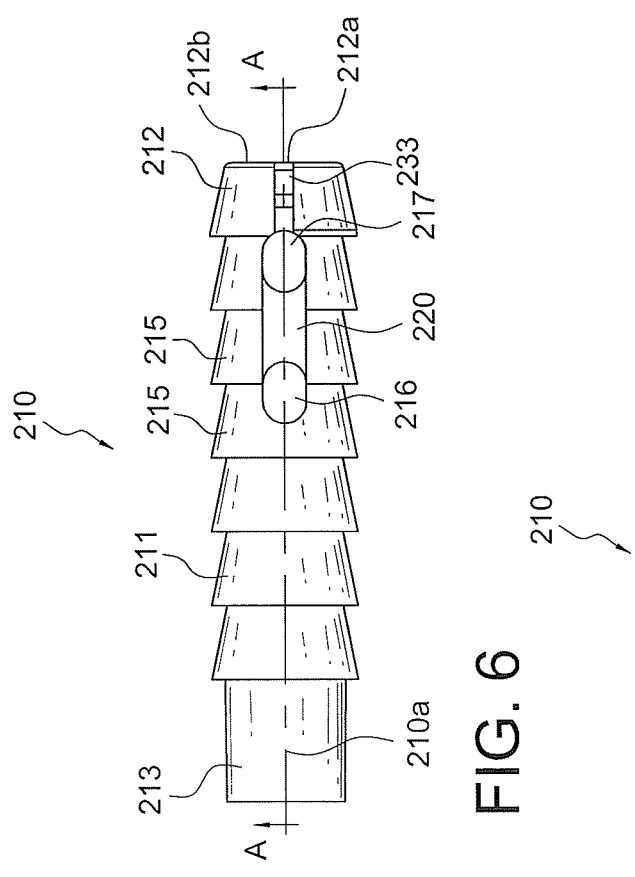
FIG. 6 illustrates a partial cross-sectional, side view of a tensionable knotless anchor according to another embodiment of the present invention.
Figure 7:
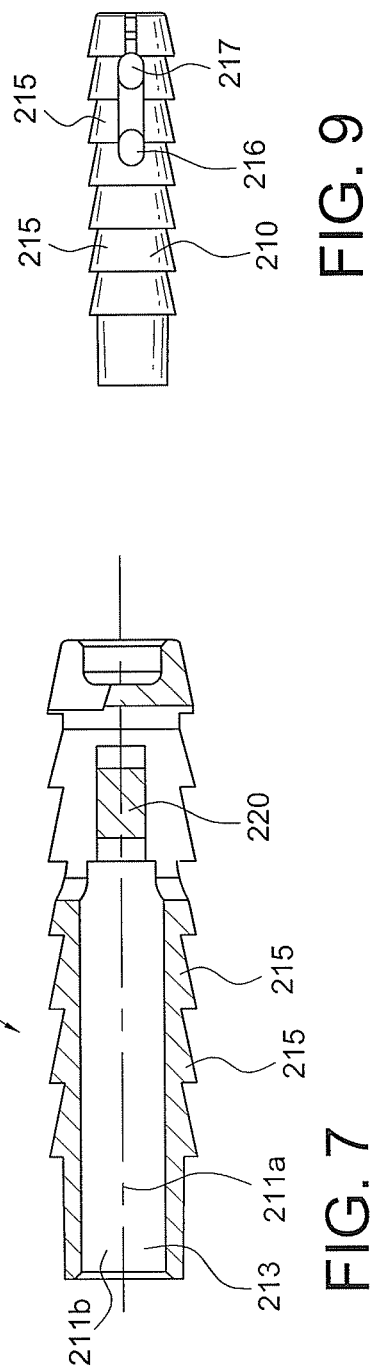
FIG. 7 illustrates a cross-sectional view of the tensionable knotless anchor of FIG. 6 (taken along line A-A').

FIGS. 6-9 illustrate various views of another tensionable knotless anchor 210 of the present invention. Tensionable knotless anchor 210 is about similar to knotless anchor 10 described above with reference to FIGS. 1-5 in that it may be used with a tensionable construct (such as construct 99 described above), but differs in that the most distal end of tensionable knotless anchor 210 is provided with a cut slot 233 that allows loading of the flexible strand 30 and suture passing device 40 onto the anchor 210. Tensionable knotless anchor 210 is provided with anchor body 211 having longitudinal axis 211a, cannulation 211b, proximal end 213 and distal end 212. Openings 216 and 217 allow threading suture(s) and/or suture passing device(s) (not shown) around post 220. Cut slot 233 is provided at most distal end of the body 210, extending from the opening 217 to a most distal end surface 212b, as shown in FIG. 6. Openings 216 and 217 are axially aligned with the cut slot 233 along longitudinal axis 211a, as shown in FIGS. 6, 7 and 9.

Although tensionable knotless anchor 210 is depicted in FIGS. 6, 7 and 9 as having ridges 215, and thus designed to be pushed into the bone, it could instead be fabricated with threads and thereby designed to be twisted or screwed into the bone.

FIGS. 10-14 illustrate surgical system 100 of FIGS. 2-5 (with knotless tensionable anchor 10, 210, suture 30 and suture passing device 40 attached to the suture 30) employed in an exemplary method of tissue repair such as a Bankart or SLAP repair, wherein the knotless suture anchor (knotless SutureTak™) simplifies arthroscopic glenohumeral joint instability repair by combining a proven and reproducible suture anchor insertion procedure with knotless soft tissue fixation.

FIG. 10 shows suture 30, preferably a UHMWPE suture, preloaded onto the anchor 10 by tying static knot 31, which prevents suture 30 from passing through distal blind hole 12a. Suture 30 is pre-attached to suture passing device 40 (for example, a FiberLink™ or a Nitinol loop 40) which is threaded through suture 30 (as shown by spliced region 39 in FIG. 10). As explained above, suture 30 is pre-loaded on anchor 10 which is loaded onto a driver (not shown in FIGS. 10-14). Suture 30 is tied to the driver (for example, wrapped around a cleft of the driver) to fasten tensionable knotless anchor 10 securely to the driver. Prior to securing knotless anchor 10 to the driver, the suture passing device 40 is attached (threaded through splice 39) to the suture 30. The construct is inserted into bone, the suture 30 untied from the driver, and the driver removed.

FIG. 10 depicts the tensionable knotless anchor 10 after it has been inserted into a drilled hole 88 in bone 80, the suture 30 released from the driver, and the driver removed. Suture 30 is passed through or around the tissue 50 which is to be reattached to bone 80. FIG. 11 depicts suture 30 passed around the tissue 50 and then threaded through eyelet/closed loop 44 of the suture passing device 40. Suture passing device 40 is pulled (as shown in FIG. 12), thereby pulling suture 30 towards tensionable knotless anchor 10.

In FIG. 13, suture 30 has been further pulled towards tensionable knotless anchor 10 so that it passed through itself inside tensionable knotless anchor 10. The suture passing device 40 has also been further pulled through suture 30. FIG. 13 illustrates surgical construct 100 with suture 30 after it has been pulled through itself, creating splice 33. The suture passing device 40 (not visible anymore in FIG. 13 as it has been completely pulled out of the suture 30) helps create splice 33 within tensionable knotless anchor 10 by facilitating suture 30 passing through itself.

Once the suture 30 has been fully passed through itself, the suture end 32 (FIG. 13) may be pulled until tissue 50 has been moved to the desired location, such as near drilled hole 88 in the bone 80. Once the desired tension and location is achieved (FIG. 14), suture end 32 may be clipped off to complete the soft tissue repair or fixation. In this manner, the suture 30 is shuttled and pulled (during the surgery) to a desired tension.

Figure 15:
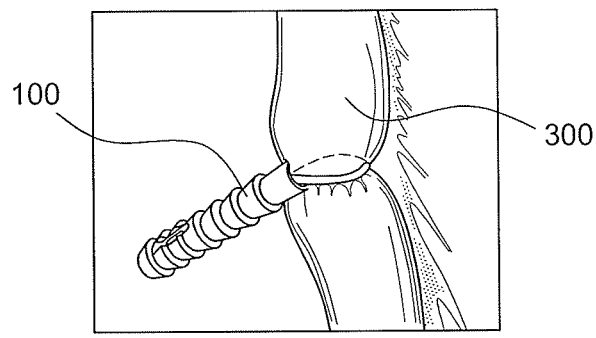
FIG. 15 illustrates the surgical construct of the present invention employed in a knotless simple stitch.

FIG. 15 illustrates surgical system 100 (with tensionable knotless anchor 10 loaded with suture passing device 40 attached to the loaded suture 30) employed in a knotless simple stitch 300.

Figure 16:
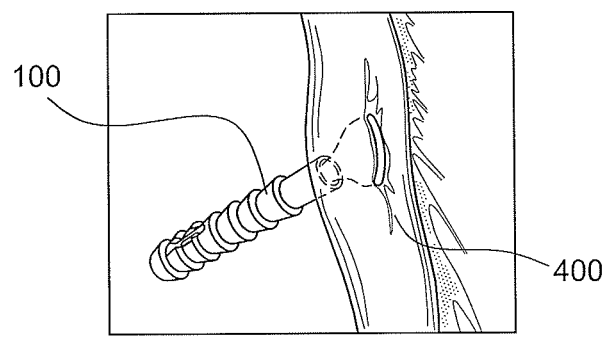
FIG. 16 illustrates the surgical construct of the present invention employed in a knotless mattress stitch.

FIG. 16 illustrates surgical system 100 (with tensionable knotless anchor 10 loaded with suture passing device 40 attached to the loaded suture 30) employed in a knotless mattress stitch 400.

FIGS. 17-29 illustrate surgical system 100 of FIGS. 2-5 (with fixation device 10, 210, flexible strand 30 and shuttling/pulling device 40 attached to the flexible strand 30) employed in another exemplary method of soft tissue repair (a Bankart and SLAP repair). A guide and drill are used to create a pilot hole precisely on the glenoid rim and the suture anchor is inserted through the same guide maintaining the same portal and drill trajectory. The knotless self-locking suture function allows the user to control the tension of the suture on the soft tissue under direct visualization.

FIGS. 17 and 18: an elevator is used to mobilize the labrum 50 on the glenoid 80. A bone socket is formed on the glenoid rim to allow subsequent insertion of surgical construct 100 of the present invention. If desired, an offset guide (FIG. 18) may be employed to aid in the placement of the anchor onto the face of the glenoid.

FIGS. 19 and 20: Surgical construct 100 is inserted into the socket in the glenoid by employing driver 90 (shown in FIG. 20). Suture 30 is released from the handle of the driver and the driver removed.

FIGS. 21-24 illustrate the passing of the suture of the surgical construct 100 around the tissue by employing suture passing and retrieving instruments known in the art (for example, a KingFisher® Suture Retriever/Tissue Grasper instrument and a SutureLasso™ instrument).

FIGS. 21 and 22: One limb of suture 30 is retrieved through the anterosuperior portal using a suture retrieval instrument 61 (for example, a KingFisher® Suture Retriever/Tissue Grasper 61). A curved SutureLasso™ instrument 62 is inserted into the anteroinferior cannula and passed through the capsulolabral tissue inferior to the anchor. Loop 63 (for example, a nitinol wire loop) is advanced into the joint. The loop is retrieved through the anterosuperior portal using the suture retrieval instrument 61.

FIGS. 23 and 24: Suture 30 is loaded through the loop 63. The wire loop 63 is retracted through the SutureLasso™ instrument 62, to pull the suture to the distal end of the SutureLasso™ instrument 62 inside the joint. The SutureLasso™ instrument 62 and the wire loop are removed together to shuttle the suture 30 through the labral tissue 50.

FIGS. 25 and 26: Suture 30 is passed through loop 44 of the suture passing device 40 (FIG. 25). The nitinol wire loop 40 is pulled away from the surgical site, to allow the suture 30 to splice itself and form splice 33 within the body of the knotless tensionable anchor 10 of system 100 (as described above with reference to FIG. 5, for example).

FIGS. 27 and 28: The free end of suture 30 is pulled until the desired tension on the repair is achieved. A knot pusher may be used when applying tension on the repair to divert the force over the anchor and steer the tissue (labrum) 50 to the desired position. The suture is cut flush with a suture cutter instrument.

FIG. 29: Final repair 500 is shown comprising a plurality of surgical constructs 100 of the present invention.

FIG. 30 illustrates a kit 600 of the present invention including a surgical construct 100 of the present invention (for example, a 3 mm knotless SutureTak) with a spinal needle, a 1.1 mm Nitinol wire 40, a portal dilator and a SutureTak drill.

Reference is now made to FIGS. 31-72, which illustrate subsequent steps of a method of assembling a surgical construct of the present invention such as surgical construct 100 of FIG. 5 (comprising a tensionable knotless anchor (knotless SutureTak) loaded with a suture and a suture passing device attached to the suture). Assembly instructions are provided below:

FIG. 31 illustrates exemplary materials for the surgical construct 100: driver 90, suture anchor 10; nitinol wire 40 with closed loop 44; and UHMWPE braid 30. The suture component 30 is constructed from exemplary braided UHMWPE.

FIG. 32 illustrates driver 90 assembled with suture anchor 10 of the present invention.

Figure 33:
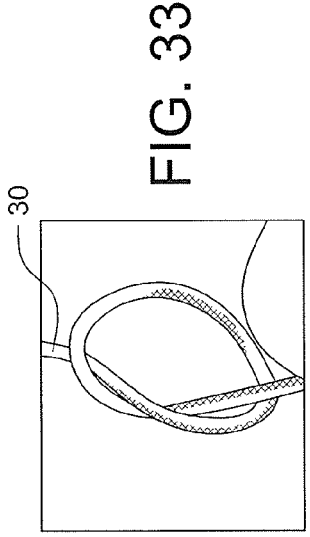

FIG. 33: Tie an overhand knot 31 within few inches from one end of the braid 30. In further steps, the sides of the knot 31 will be referred to as the short end and the long end (resembling the length of suture 30 on the particular side of the knot). Preferably, there should be no tipped suture within the vicinity of the knot.

Figure 34:
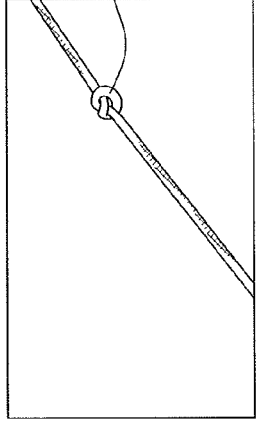

FIG. 34: Pull knot 31 tight so that the knot will fit in hole of the anchor.

Figure 35:
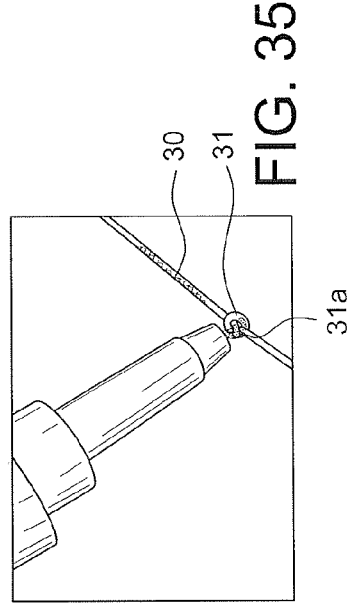

FIG. 35: Optionally, place a small amount of bonding agent 31a on the knot 31.

Figure 36:
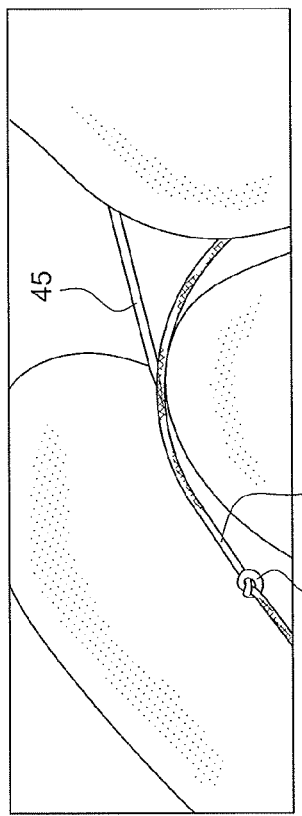

FIG. 36: Perform the next steps with a straight needle 45 with an attached nitinol loop 40. Any alternative suture passing device may be used as long as it allows the formation of the device 100 in FIG. 43. Pierce the braid 30 with the needle 45 at a predetermined distance from the long end of the knot 31.

Figure 37:
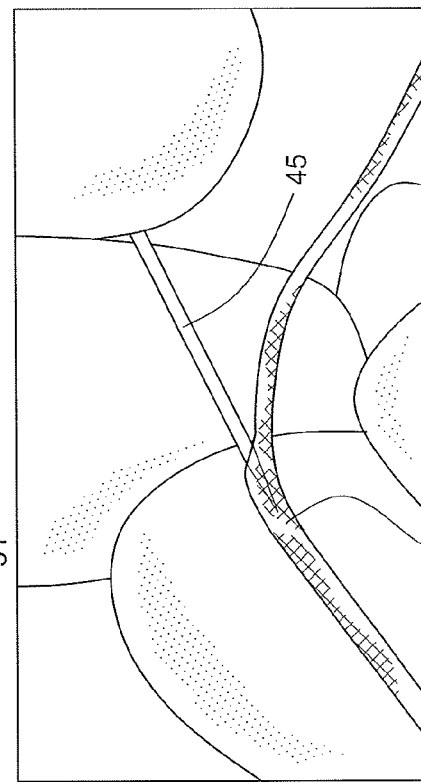

FIG. 37: Advance the needle 45 through the center of the braid 30, taking care not to penetrate the sheath with the tip of the needle.

FIG. 38: Allow needle 45 to exit the sheath 30 a distance from the knot 31. The needle must not be passed through glued portions of the braid 30.

FIG. 39: Pass a small length of suture 71 through the open end 44 of the nitinol wire 40.

FIG. 40: Pass both free ends of the suture 71 through the loop 45a on the needle 45 and fold the ends.

FIG. 41: Advance the needle 45 through the sheath 30 so the folded suture ends are passed through the center of the braid 30.

FIG. 42: Continue to pull the suture 71 through the braid 30 resulting in pulling the nitinol wire 40 through the center of the braid 30 as well.

Figure 43:
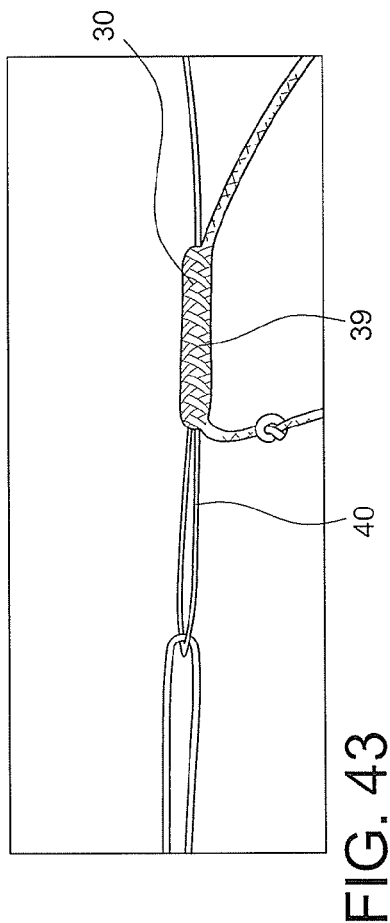

FIG. 43: Pull approximately half of the nitinol wire 40 through the braid splice 39. Ensure the shrink tube of the nitinol wire does not snag any portion of the splice 39.

Figure 44:
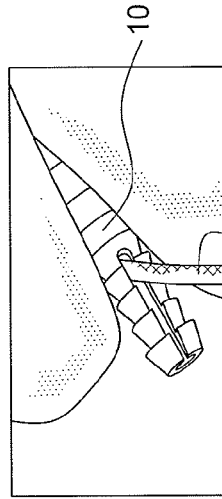

FIG. 44: Insert the long free end of the braid 30 into the side port of the anchor 10 that is on the same side as the cut slot (for example, cut slot 233).

Figure 45:
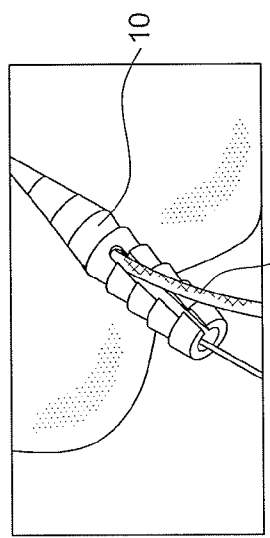

FIG. 45: Pull the braid 30 through the end hole.

Figure 46:
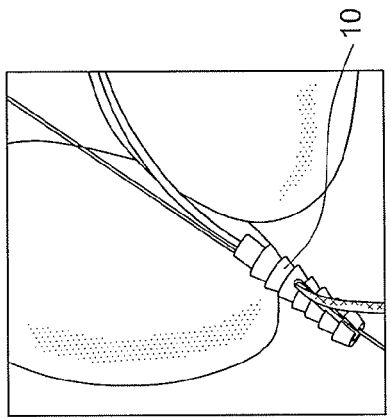

FIG. 46: Insert the non-looped end of the nitinol wire 40 through the same side port as the braid 30.

Figure 47:
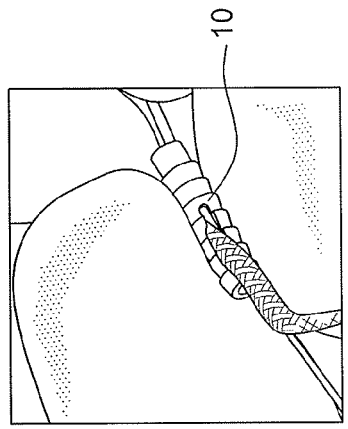

FIG. 47: Pull the nitinol 40 and the braid 30 evenly through the anchor 10 so the splice passes through the side port. Pass the splice 39 until there is sufficient access to the through hole across the side ports.

Figure 48:
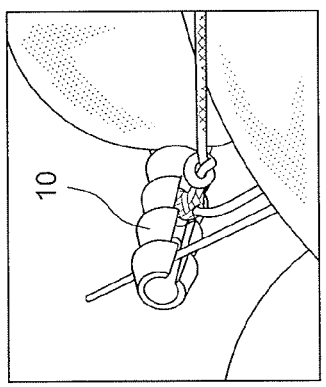

FIG. 48: Pass the looped end of the nitinol wire 40 through the side port access hole to the other side of the anchor. Pull until slack is removed.

Figure 49:
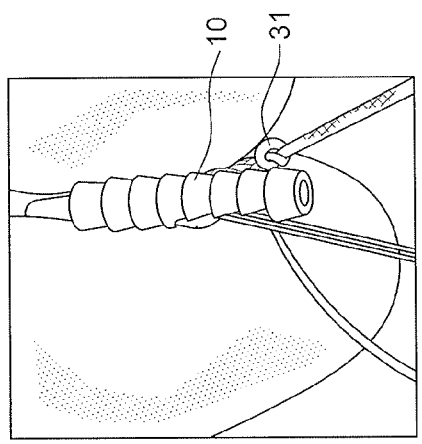

FIG. 49: Insert looped end of nitinol wire 40 back into side port and out the end hole.

Figure 50:
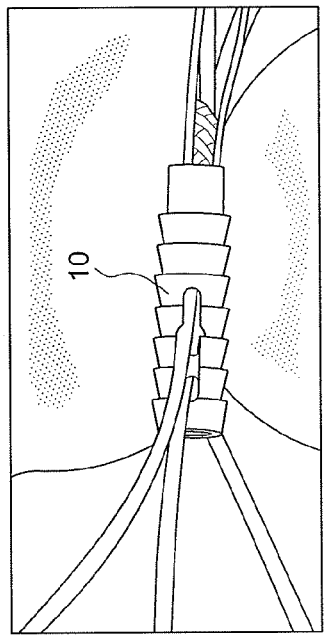

FIG. 50: Looped end of nitinol wire 40 should be on the opposite side of the post than the splice.

Figure 51:
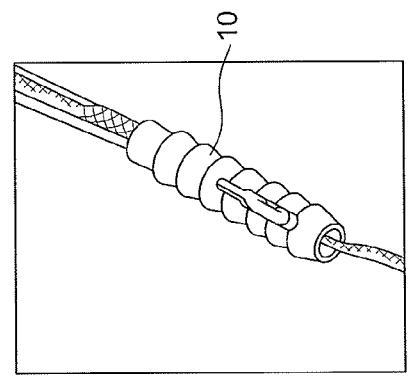

FIG. 51: Feed wire to remove all slack within and around the anchor.

Figure 52:
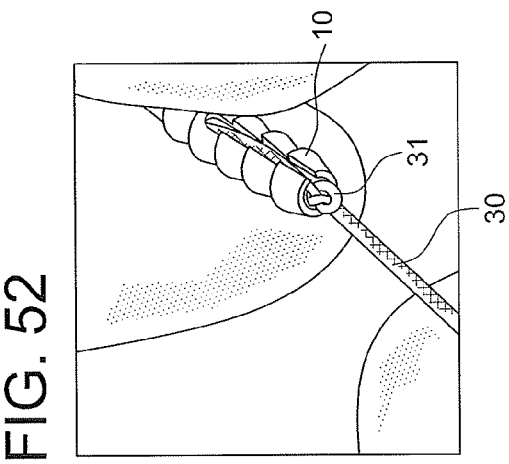

FIG. 52: Pull short end of braid 30 and knot 31 and relocate it through the cut slot 233 of the anchor.

Figure 53:
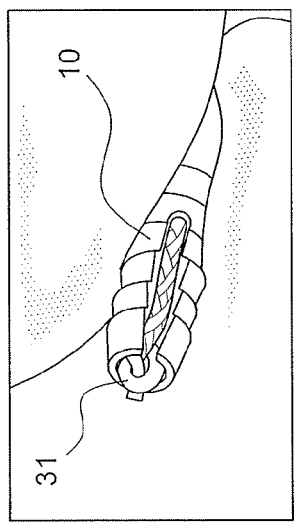

FIG. 53: Pull long end of braid 30 to seat knot 31 within the counterbore of the tip. Cut the remainder of the short end.

Figure 54:
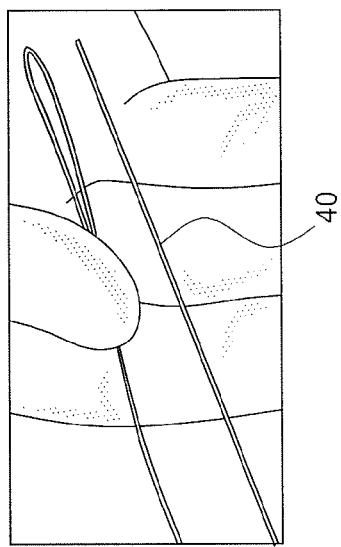

FIG. 54: Nitinol wire 40 should pull freely in both directions through the anchor 10 and braid splice 39. Adjust wire so both ends are about even.

Figure 55:
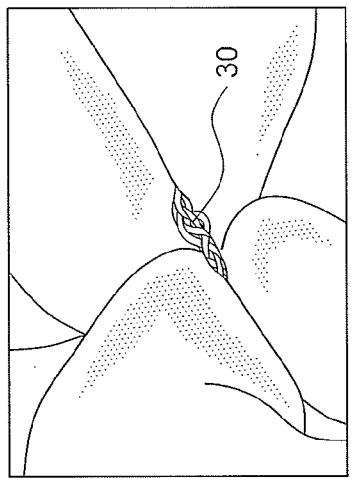

FIG. 55: From the end of the suture tail, pinch the suture 30 and compress it, to loosen the yarns within the braid.

Figure 56:
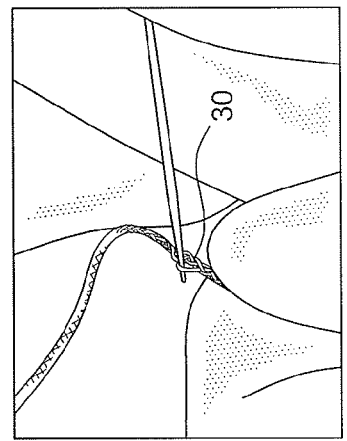

FIG. 56: With a needle, separate one of the yarns.

Figure 57:
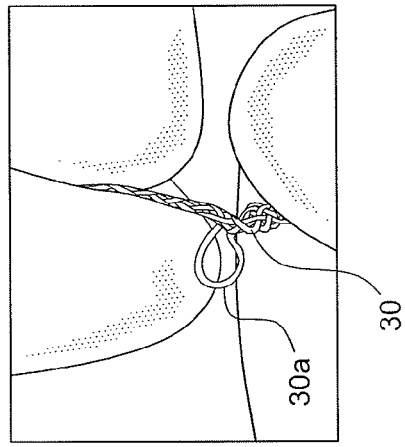

FIG. 57: Lightly pull some slack to form a small loop 30a.

Figure 58:
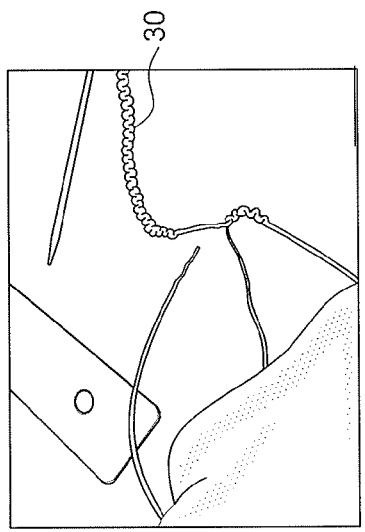

FIG. 58: Carefully pull the yarn from the direction of the free suture end out from the braided suture. The braid may wrinkle as a result. Limit the amount of wrinkling in the opposite direction of the free end by limiting pulling of the yarn from that direction.

Figure 59:
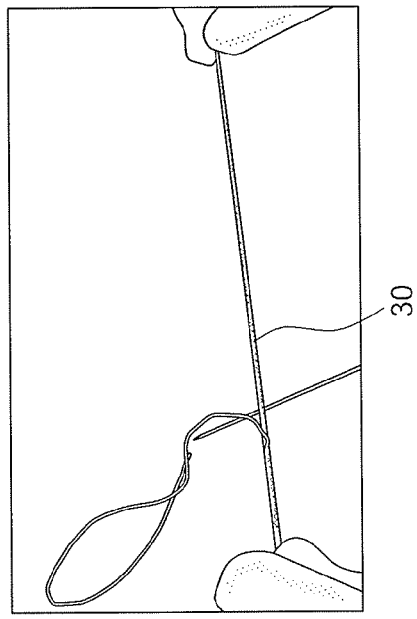

FIG. 59: Once the yarn is removed, the suture can be straightened out and smoothened, by pinching it with the finger and running it along the direction of the free end. This step is optional.

Figure 60:
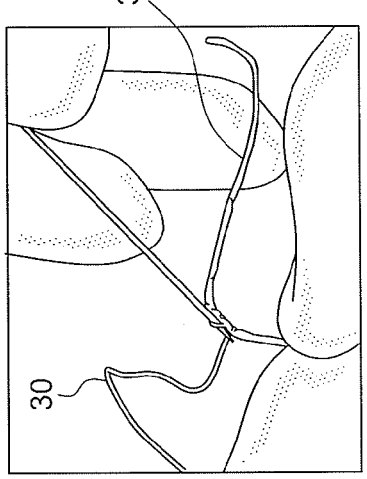

FIG. 60: Using the needle, separate out a second yarn from the site of the first yarn.

Figure 61:
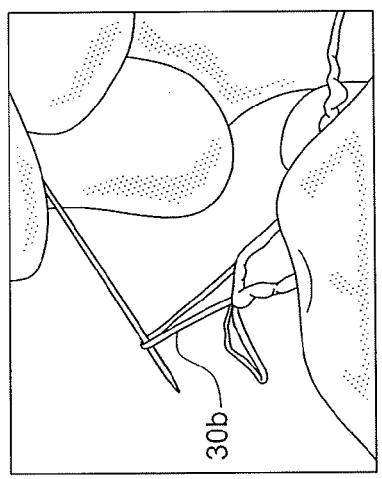

FIG. 61: Lightly pull some slack to form a small loop 30b.

Figure 62:
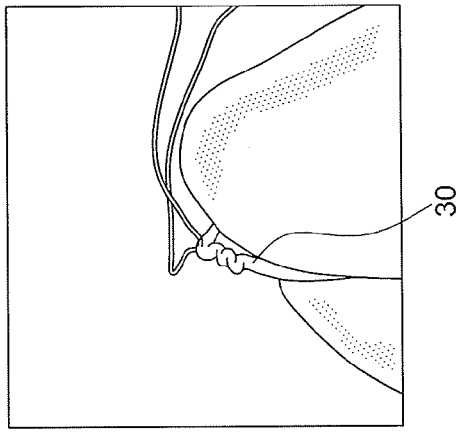

FIG. 62: Carefully pull the yarn from the direction of the free suture end out from the braided suture. The braid may wrinkle as a result. Limit the amount of wrinkling in the opposite direction of the free end, by limiting pulling of the yarn from that direction.

Figure 63:
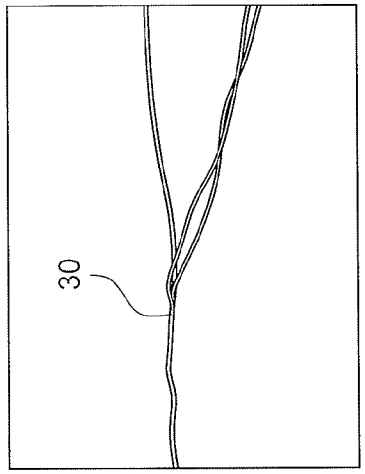

FIG. 63: Once the yarn is removed the suture can be straightened out and smoothened. The result should be similar to the picture with two loose yarns branching off from the larger.

Figure 64:
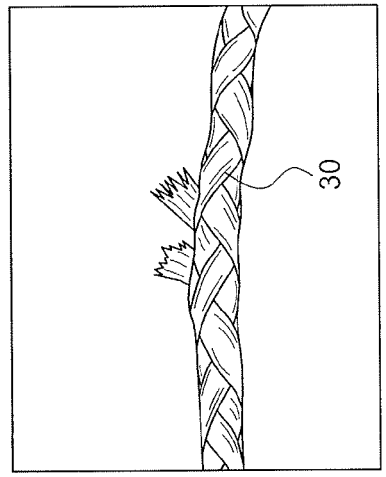

FIG. 64: The loose yarns shall be carefully trimmed close to the surface of the larger suture. The frayed edges should be pinched with the suture and brushed in the direction of the loose end, to limit how much it sticks out. Optional: step may be performed before smoothening the suture to facilitate blending the cut ends in.

Figure 65:
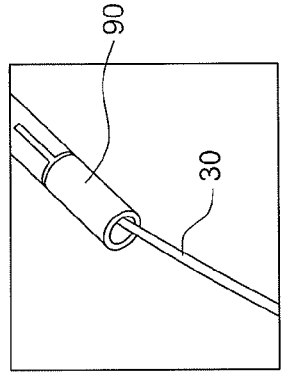

FIG. 65: Ensure there are no knots on the free end of the braid. Feed the free end of braid into the opening of the driver 90, until it can be pulled from the opposite side.

Figure 66:
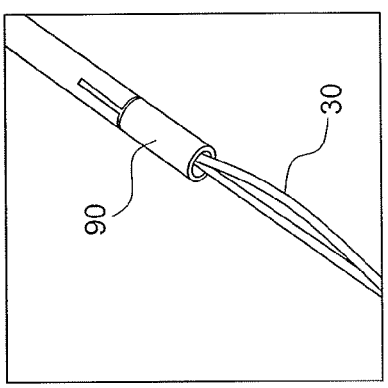

FIG. 66: Insert both ends of the nitinol wire 40 into the opening of the driver 90.

Figure 67:
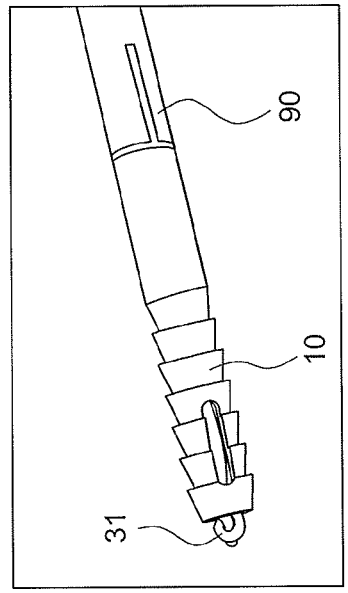

FIG. 67: Pull the slack of the braid 30 and the nitinol 40 so the anchor 10 seats in the counterbore of the driver 90.

Figure 68:
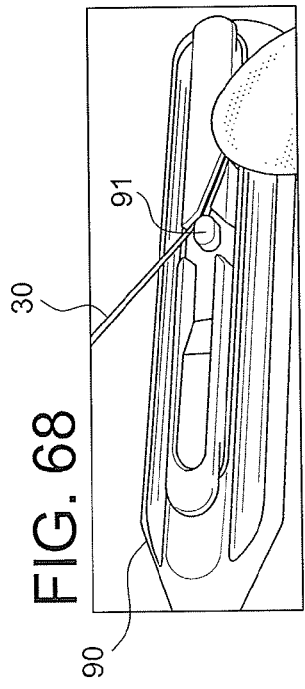

FIG. 68: Wrap the free end of the braid clockwise around keel 91 of the driver 90 once. Then pass it through the keel as shown.

Figure 69:
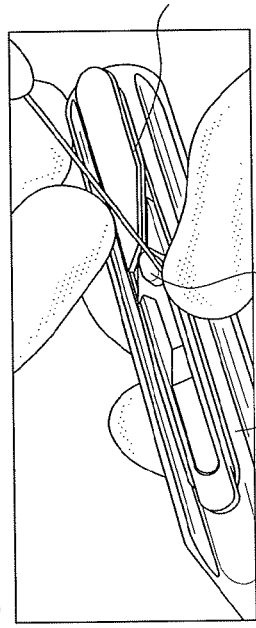

FIG. 69: Continue to pass the braid halfway around the keel counterclockwise.

Figure 70:
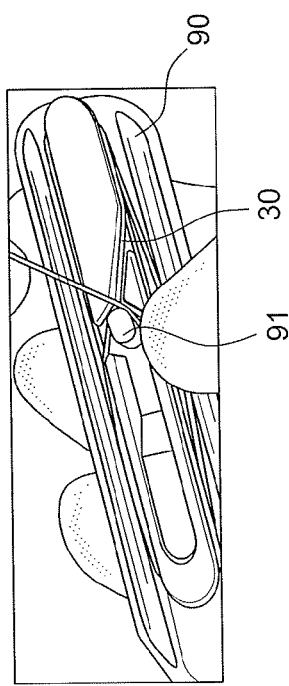

FIG. 70: Pass the braid back through the keel as shown.

Figure 71:
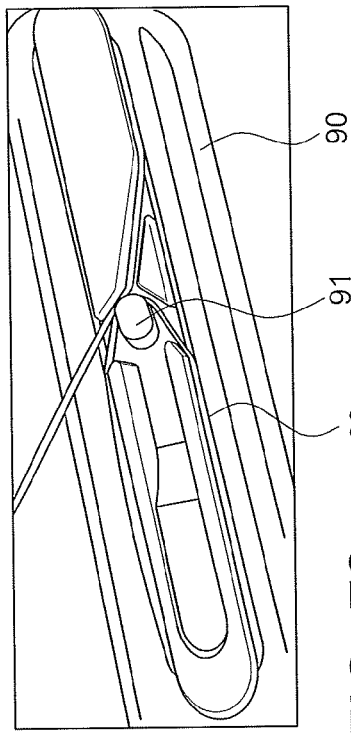

FIG. 71: Result should look as shown. A length of braid 30 should extend from keel 91. Trim excess braid (there should not be any tipped suture left on the end).

Figure 72:
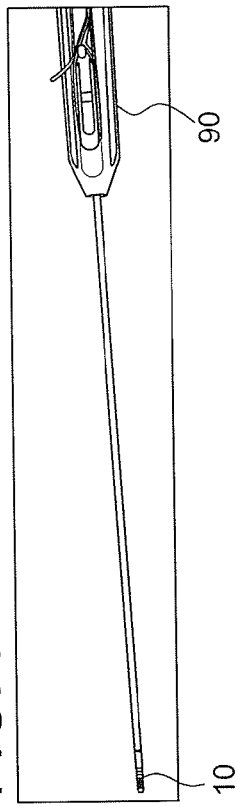

FIG. 72: Completed final assembly.

FIGS. 73-77 illustrate other exemplary embodiments of self-cinching tensionable knotless anchor 310, 310a of the present invention that allow for knotless soft tissue repairs. Tensionable knotless anchor 310, 310a has a new design that allows for a significantly smaller diameter anchor to be used (i.e., less than a 3 mm anchor). This knotless anchor uses a mechanism similar to that of the SutureTak™ which is disclosed and described in U.S. Provisional Appl. No. 61/663,024 entitled "Tensionable Knotless Labral Anchor and Methods of Tissue Repair," filed on Jun. 22, 2012, the disclosure of which is incorporated by reference in its entirety herein.

The final splice mechanism 221 (FIG. 77) of surgical construct 200 (FIG. 77) is located outside the anchor 310a but within the drill hole 88. The suture 30 does not travel around a post to lead into the splice (as in the previously-described embodiments) but rather passes through a cannulation of the anchor body and fixed to the anchor by knot 31. The anchor 310, 310a is significantly shorter in length and diameter. The final splice construct 221 (FIG. 77) is contained in bone 80 (within bone socket or hole 88) but not within the anchor 310, 310a.

Figure 73:
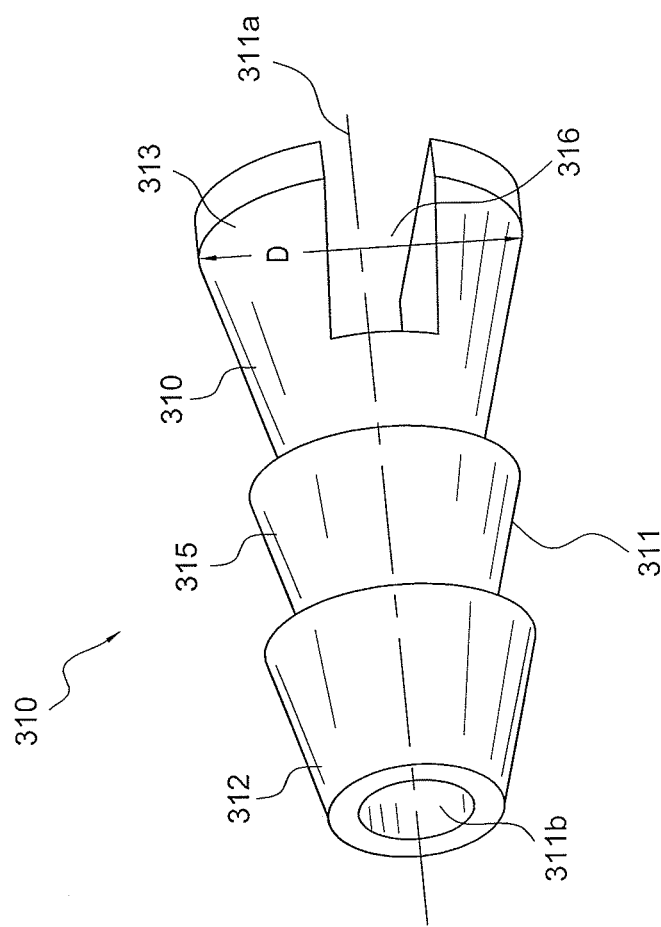
FIG. 73 illustrates a tensionable knotless anchor according to another exemplary embodiment of the present invention.

Tensionable knotless anchor 310 of FIG. 73 is about similar to knotless anchors 10, 210 described above in that it may be used with a tensionable construct (such as construct 99 described above), but differs in that anchor body 311 of anchor 310 is very small (i.e., with outer diameter D of less than 3 mm) and provided with only three exemplary ridges 315. Anchor body 311 is also provided with a longitudinal axis 311a, cannulation 311b, proximal end 313 and distal end 312. Opening 316 (located at the most proximal end) allows threading suture(s) and/or suture passing device(s) (not shown) around a post or similar structure (not shown) located within the body 311. Opening 316 extends along the longitudinal axis 311a, as shown in FIG. 73 and may have various geometries and configurations, for example, the rectangular shape shown in FIG. 73 (extending from one outer side of the anchor body to the diametrically-opposed outer side of the body).

Although tensionable knotless anchor 310 is depicted in FIG. 73 as having ridges 315, and thus designed to be pushed into the bone, it could instead be fabricated with threads and thereby designed to be twisted or screwed into the bone.

FIGS. 74-77 illustrate an exemplary method of anchoring surgical construct 200 of the present invention which includes tensionable anchor 310a assembled with construct 99 (tensionable construct 99) formed of flexible strand or flexible material 30 (suture 30 or tie down suture 30) and shuttle/pull device 40 (suture passing instrument such as FiberLink™ 40 or a nitinol loop 40) attached to the flexible strand 30. Tensionable anchor 310a of FIGS. 74-77 is similar to tensionable anchor 310 of FIG. 73 but differs in that the anchor body is not provided with rectangular opening 316 and the flexible material does not pass around a post or a similar structure.

Figure 74:
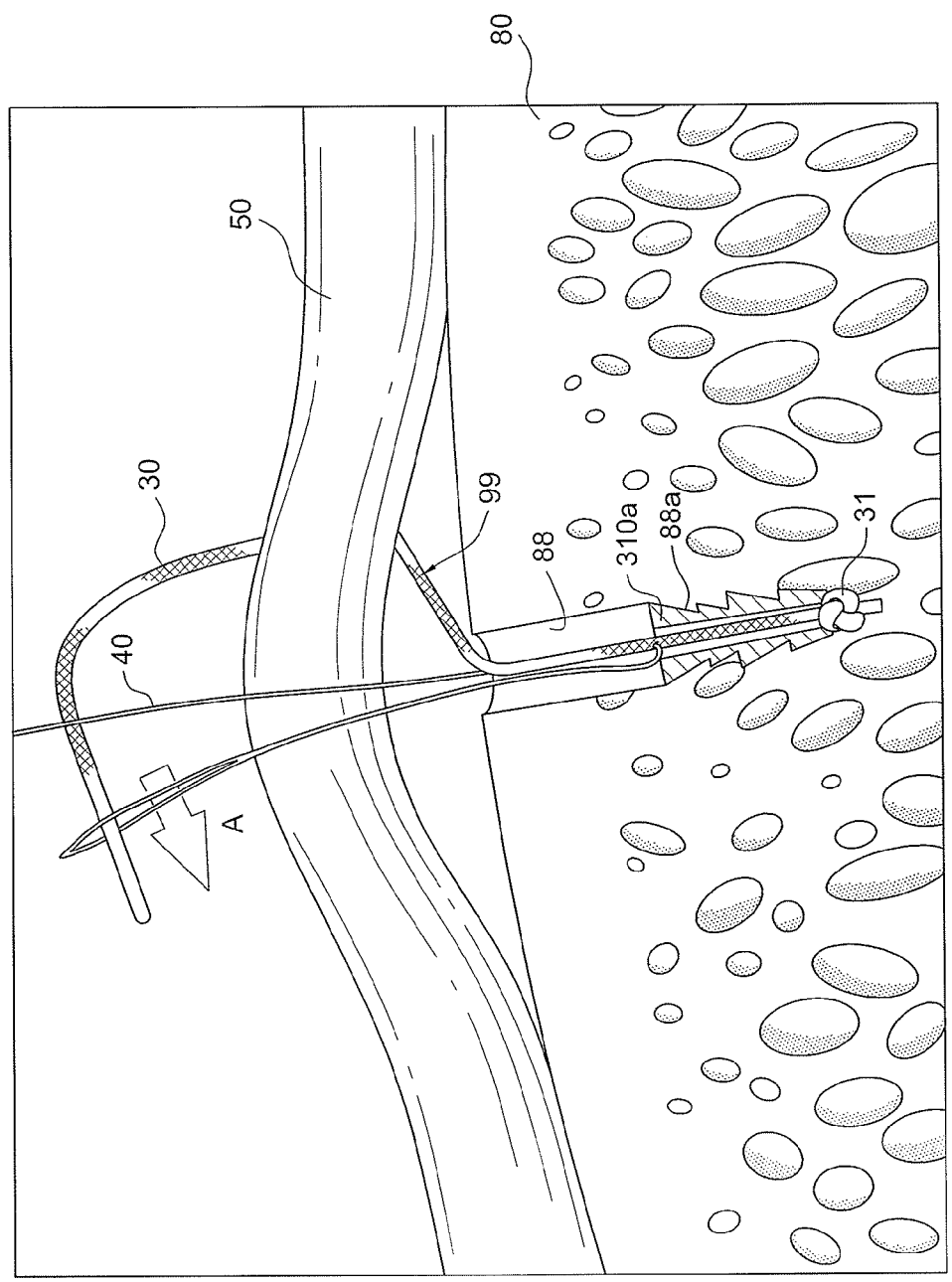
FIG. 74 is a cross-sectional view of a surgical construct according to another exemplary embodiment of the present invention (with the knotless tensionable anchor of FIG. 73 and with a suture and a suture passing device attached to the suture, before tensioning of the suture).

In this exemplary embodiment, and as shown in FIGS. 74-77, the final splice 221 is located outside the anchor body of tensionable anchor 310a but within the bone tunnel or socket 88. An exemplary method of anchoring surgical construct 200 comprises the steps of:

FIG. 74: Anchor 310a is implanted in stepped bone tunnel 88. The bone tunnel 88 may be larger than tunnel 88a where the anchor rests, to accommodate the suture splice construct. The anchor 310*a* is preloaded with splice making mechanism 221.

Figure 75:
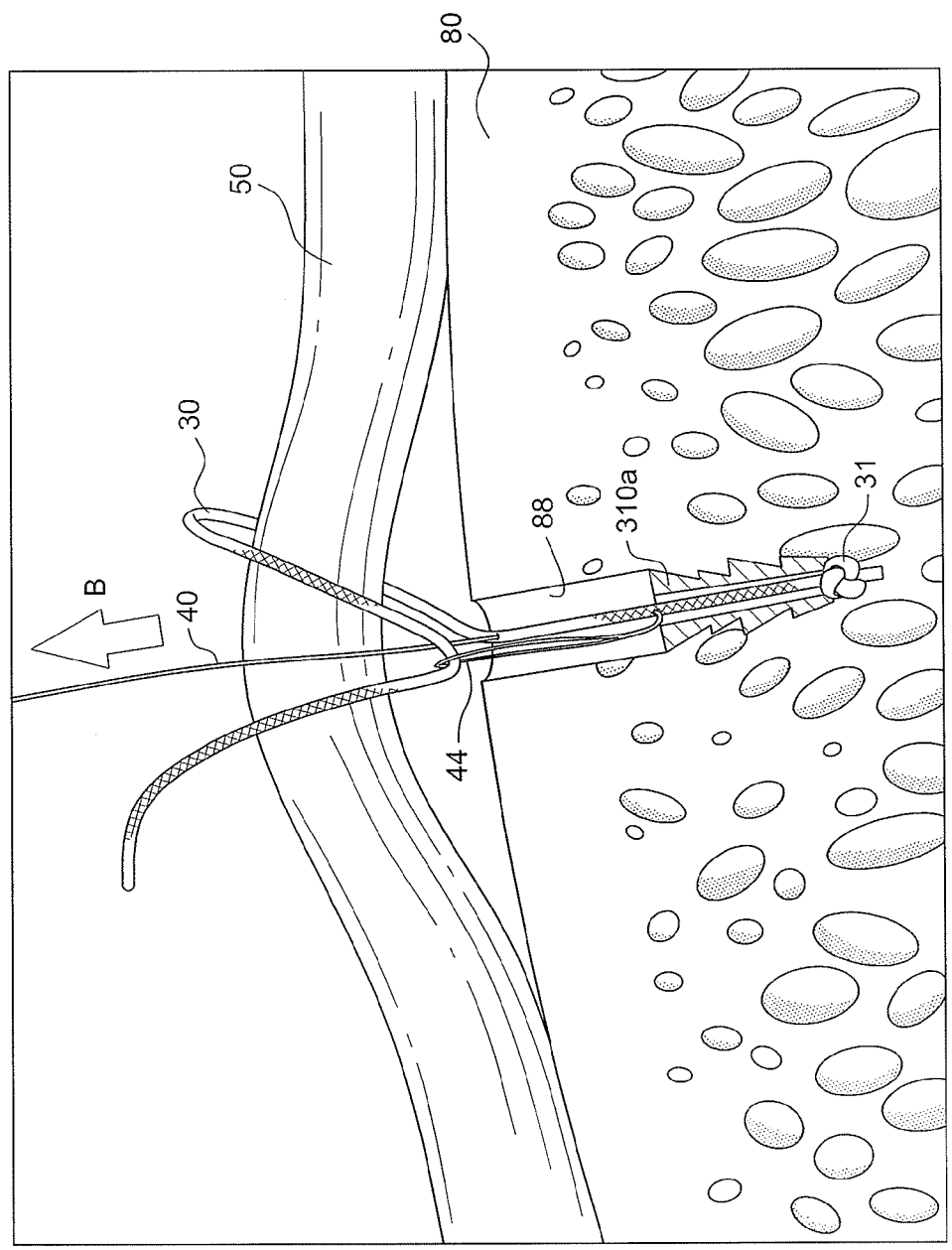
FIG. 75 illustrates the surgical construct of FIG. 74 with the suture threaded through the suture passing device.

FIG. 75: Similar to the previous design, the suture is passed around the tissue 50 and is loaded through the shuttling/pulling device 40 (Nitinol wire 40). Nitinol wire 40 is pulled to shuttle the suture 30.

Figure 76:
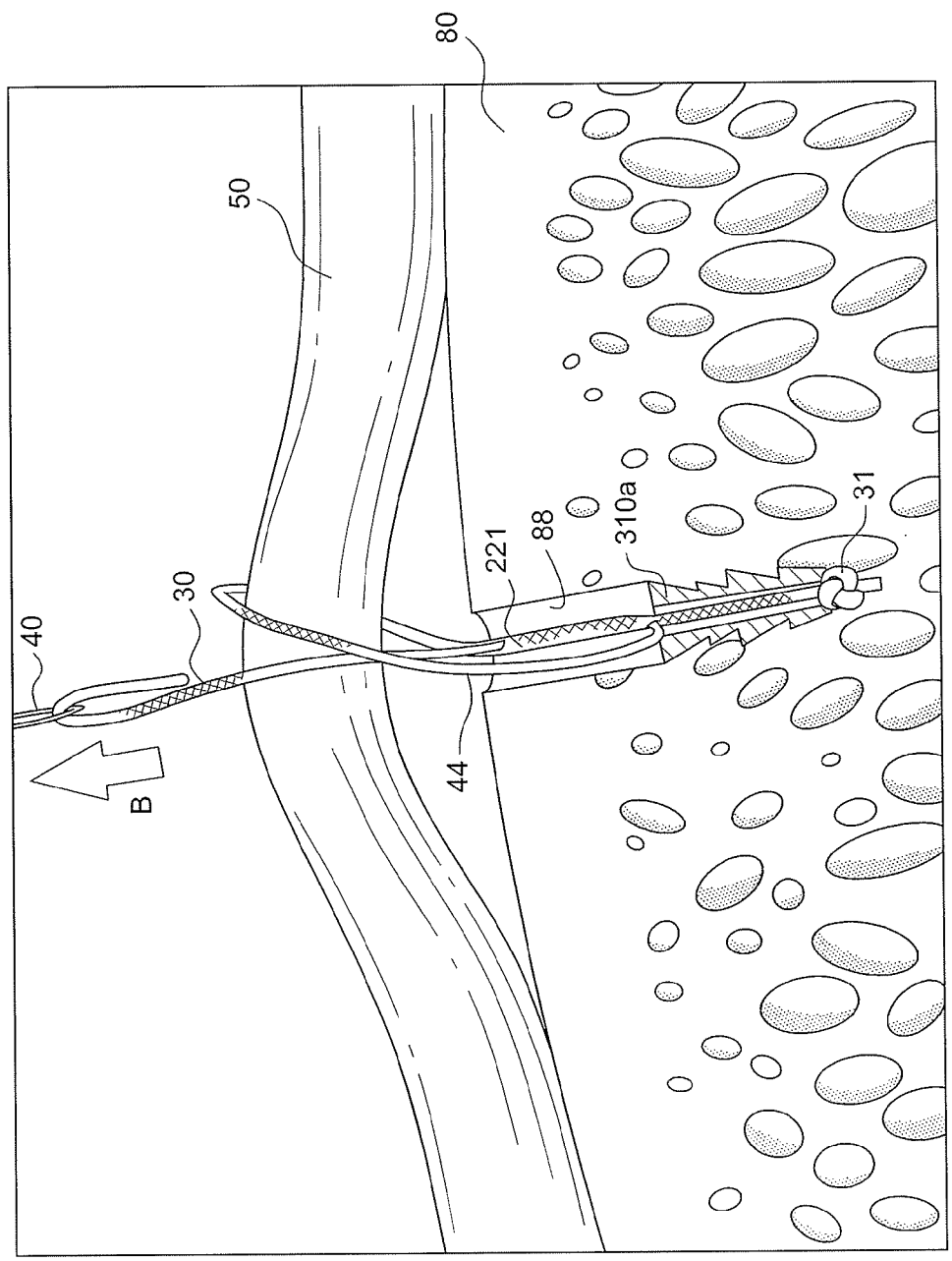
FIG. 76 illustrates the surgical construct of FIG. 75 during tensioning, wherein the suture has been pulled so that the suture passes through itself.

FIG. 76: Similar to the previous design, suture 30 is shuttled through itself to create a splice 221 with the nitinol loop 40. There is no "lead-in" from a post, but the suture can be tapered to help facilitate pulling it through.

Figure 77:
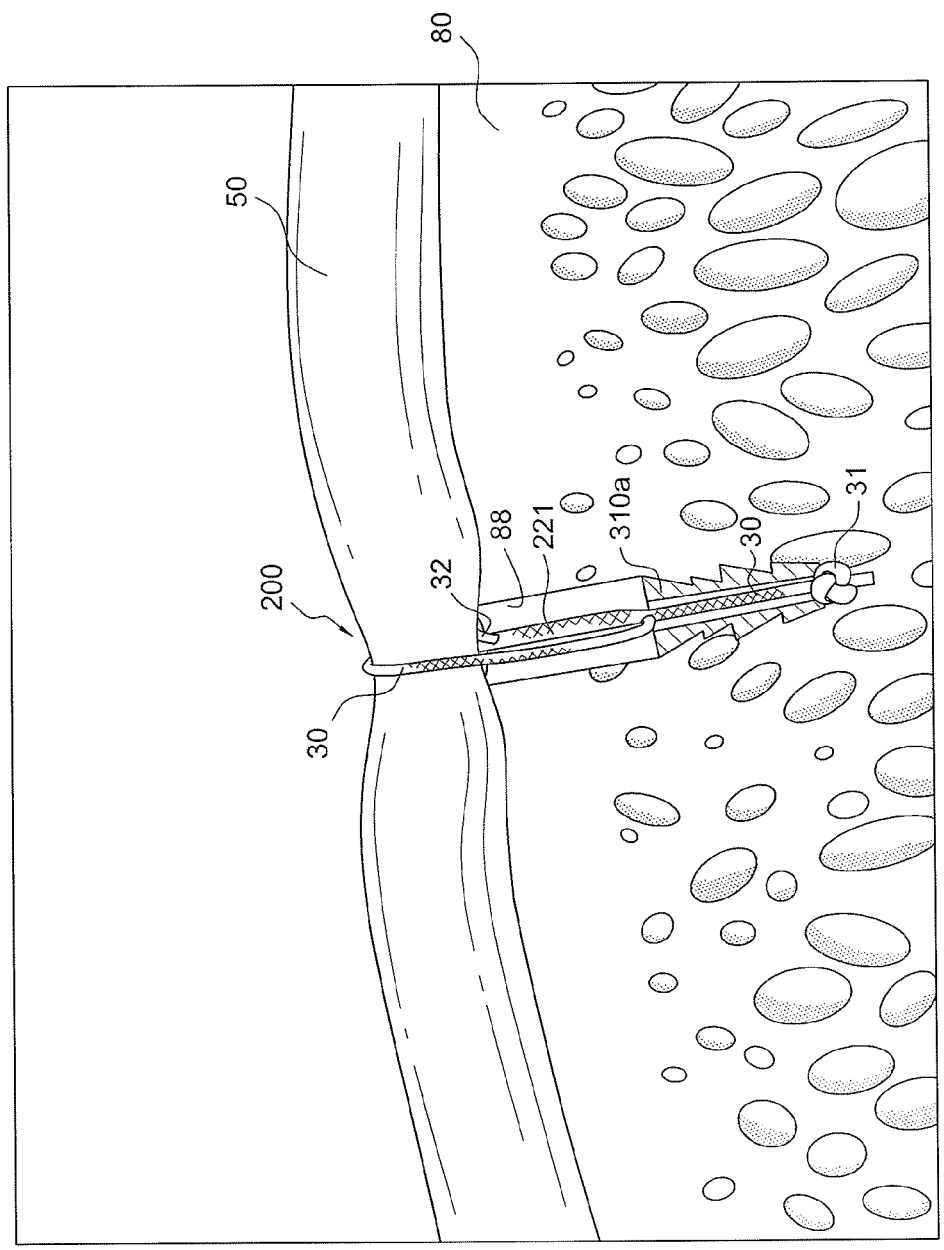
FIG. 77 illustrates the surgical construct of FIG. 76 after tensioning, wherein the suture has been pulled through itself to create a splice and the tissue has been pulled towards the bone.

FIG. 77: Same as in the previous design, the suture 30 is pulled until the tissue 50 has been moved to the desired location relative to the bone 80, and the desired tension and location have been achieved. Tension makes mechanism work and suture 30 is trimmed.

An exemplary method of tissue repair with surgical construct 200 (including tensionable anchor 310, 310*a*, flexible material 30 and passing device 40) comprises inter alia the steps of: (i) providing a surgical construct 99 comprising a fixation device 310*a* (for example, anchor) with a flexible strand 30 (for example, suture) fixed to the fixation device 310*a* (by knot 31, for example) and with a shuttle/pull device 40 (a suture passing instrument) attached to the flexible strand 30; (ii) inserting the fixation device 310 into bone; (iii) passing the flexible strand 30 around or through tissue to be fixated (or reattached) to bone, and then through an eyelet/loop of the shuttle/pull device 40; (iv) subsequently, pulling on the shuttle/pull device 40 to allow the flexible strand 30 to pass through itself and to form a splice 221 outside of the body of the fixation device (with the flexible strand passing through itself); and (v) pulling on the flexible strand to allow the soft tissue to achieve the desired location relative to the bone, and to allow proper tensioning of the final construct.

Figure 78:
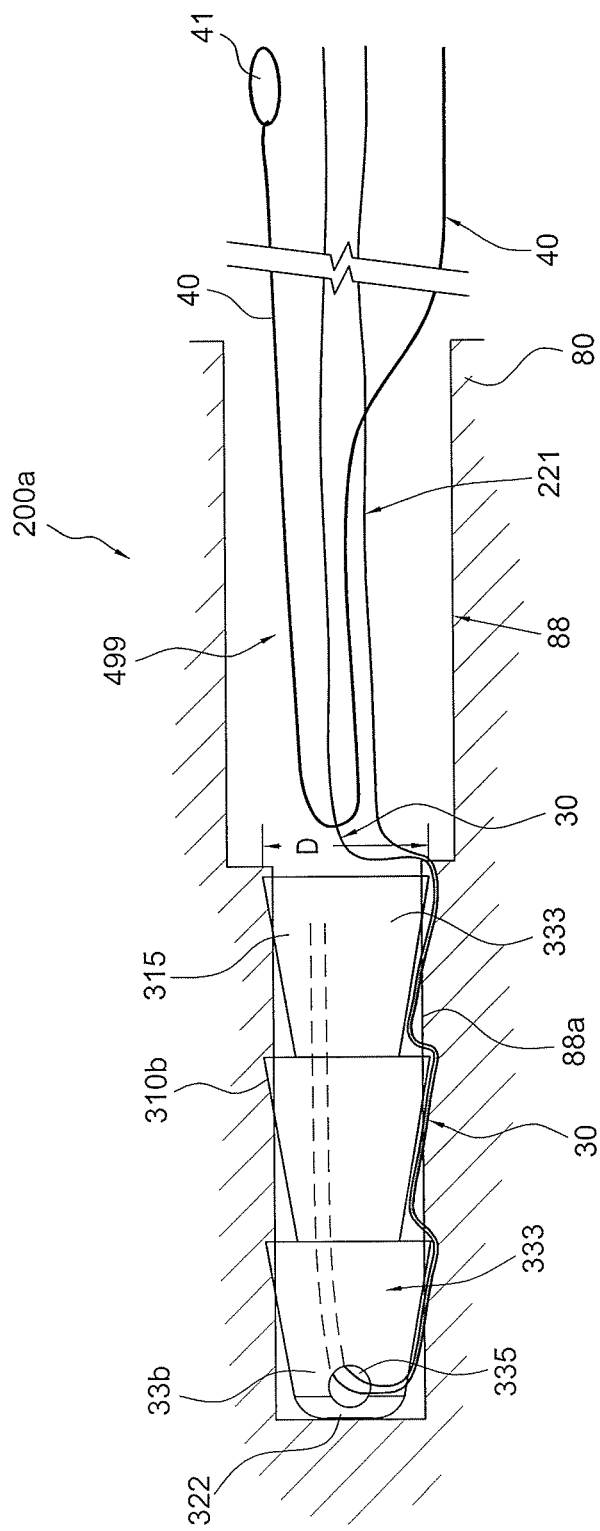
FIG. 78 illustrates a partial, cross-sectional view of a surgical construct according to another embodiment of the present invention (with a knotless tensionable anchor and a suture mechanism contained within the bone and outside of the body of the knotless tensionable anchor).

FIG. 78 illustrates another exemplary embodiment of a surgical construct 200*a* according to yet another embodiment of the present invention. The surgical construct 200*a* comprises a knotless tensionable anchor 310*b* and a suture mechanism 499 (similar to tensionable construct 99) that is contained within the bone and outside of the body of the knotless tensionable anchor. According to this exemplary-only embodiment, the suture end is fixed to the anchor body (which may be solid or cannulated) by overmolding the suture to the anchor body or by compressing the suture against the bone (i.e., similarly to how a PushLock® anchor (disclosed in U.S. Pat. No. 7,329,272, the disclosure of which is incorporated by reference in its entirety herewith) fixes suture into a bone tunnel or socket).

The knotless tensionable anchor 310*b* of FIG. 78 is similar to the designs of the anchors 310, 310*a* of FIGS. 73-77 in that it is also a significantly smaller diameter anchor (i.e., less than a 3 mm anchor) and uses a mechanism similar to that of the SutureTak™ which is disclosed and described in U.S. Patent Appl. Publication No. 2013/034575061, the disclosure of which is incorporated by reference in its entirety herein. However, the suture mechanism 499 (formed of flexible strand 30 and shuttle/pull device 40 attached to the flexible strand 30) is not attached to the anchor by a knot, but rather it is affixed to the body of the anchor (fixed to it) by being trapped between the anchor and bone. For this, the anchor body needs not be cannulated and could be instead a solid body (or a partially solid body).

Tensionable anchor 310*b* of FIG. 78 is also provided with an anchor body 333 which is very small (i.e., with an outer D of less than 3 mm) and with only three exemplary ridges 315. Anchor body 333 is also provided with a longitudinal axis 322, a proximal end 333*a* and distal end 333*b*. Opening 335 (located at the most distal end) allows threading suture(s) 30 and/or suture passing device(s) 40 to pass therethrough and aid in the fixation of the suture 40 to the anchor body 333. Opening 335 may extend about perpendicular to the longitudinal axis 332 and may have a circular configuration, as shown in FIG. 78, but may have other geometries and configurations, and may be located in other directions relative to the longitudinal axis of the anchor body. Anchor body 333 may be solid or cannulated.

Upon insertion into bone socket or tunnel 88 in bone 80, the suture mechanism forms the splice 221 similar to those formed in the above-described embodiments (i.e., with flexible strand 30 and shuttle/pull device 40 attached to the strand 30 and in a manner similar to the formation of the final constructs described above). However, splice 221 is contained within the bone 80 instead of the anchor body. As shown in FIG. 78, suture 30 is fixed to anchor body 333 either by overmolding the suture to the anchor, or by compressing the suture against the walls of bone tunnel or socket 88 in a manner similar to how a PushLock® anchor (disclosed in U.S. Pat. No. 7,329,272, the disclosure of which is incorporated by reference in its entirety herewith) fixes suture into a bone tunnel or socket.

An exemplary method of tissue repair employing anchor 310*b* of FIG. 78 comprises inter alia the steps of: (i) providing a fixation device 310*b* (for example, an anchor) with a flexible strand 30 (for example, suture) fixed to the fixation device and with a shuttle/pull device 40 (a suture passing instrument) attached to the flexible strand 30; (ii) inserting the fixation device 310*b* into a tunnel 88*a* in bone 80; (iii) passing the flexible strand 30 around or through tissue to be fixated (or reattached) to bone, and then through an eyelet/loop of the shuttle/pull device 40; (iv) subsequently, pulling on the shuttle/pull device 40 to allow the flexible strand 30 to pass through itself and to form a splice 221 outside of the body of the fixation device 310*b* (with the flexible strand passing through itself) but within tunnel 88 of the bone 80; and (v) pulling on the flexible strand 30 to allow the soft tissue to achieve the desired location relative to the bone, and to allow proper tensioning of the final construct.

Anchor 310, 310*a*, 310*b* may be formed of metal, biocompatible plastic such as PEEK or a bioabsorbable PLLA material. The anchors may be provided with a socket at the distal end (such as socket 19 of the anchor 10) configured to securely engage a tip of a driver. The socket of the anchor 310, 310*a*, 310*b* may have any shape adapted to receive a driver tip for pushing the anchors, for example, tap-in or screw-in style anchors. Tensionable knotless anchor 310, 310*a*, 310*b* may be made of one or more pieces, or may be provided as an integrated device.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329, 272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The strands may also be formed of a stiff material, or combination of stiff and flexible materials, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A method of tissue repair, comprising the steps of:
installing a fixation device in bone, the fixation device comprising a body, a flexible strand extending through at least a portion of the body and a shuttling device passing through a splice region of the flexible strand;
after installing the fixation device in bone, passing an end of the flexible strand around or through soft tissue to be fixated, and then attaching the end of the flexible strand to the shuttling device;
pulling on an opposite end of the shuttling device to pull the end of the flexible strand through the splice region of the flexible strand, thereby forming a knotless closed loop having an adjustable perimeter.

2. The method of claim 1, wherein the splice region is located within the body of the fixation device.

3. The method of claim 1, wherein the splice region is located outside of the body of the fixation device.

4. The method of claim 1, wherein the flexible strand extends through a cannulation of the body of the fixation device.

5. The method of claim 1, wherein the flexible strand extends through an opening at a most distal end of the body of the fixation device.

6. The method of claim 1, wherein the body of the fixation device is solid.

7. The method of claim 1, further comprising the step of adjusting the length of the knotless closed loop to approximate tissue to bone.

8. A method of tissue repair, comprising the steps of:
providing a surgical device comprising a fixation device and a flexible construct, the flexible construct comprising a flexible strand and a shuttling/pulling device attached to the flexible strand;
installing the fixation device into bone;
passing the flexible strand around or through soft tissue to be fixated, and then through an eyelet of the shuttling/pulling device; and
pulling on the shuttling/pulling device such that the flexible strand forms a splice through itself, and provide tensioning of the tissue to be fixated relative to the bone.

9. The method of claim 8, wherein the splice is formed within the fixation device.

10. The method of claim 8, wherein the splice is formed outside the fixation device.

11. The method of claim 8, further comprising the steps of:
pre-loading the fixation device with the flexible construct;
securing the fixation device to a driver by tying the flexible strand to the driver;
inserting the fixation device into a hole in the bone;
passing the flexible strand through or around the soft tissue to be fixated;
subsequently, threading the flexible strand through an eyelet of the shuttling/pulling device; and
pulling on the shuttling/pulling device such that the flexible strand is spliced through itself to create an adjustable knotless loop for approximating the soft tissue to the bone.

12. The method of claim 8, wherein the fixation device is a knotless anchor.

13. The method of claim 8, wherein the flexible strand is a suture formed of ultrahigh molecular weight polyethylene.

14. The method of claim 8, wherein the shuttling/pulling device is a nitinol wire.

15. A method of tissue repair, comprising the steps of:
installing a fixation device and a flexible construct in bone, the fixation device comprising a cannulated body, a longitudinal axis, a proximal end, and a distal end, the flexible construct being attached to the fixation device and comprising a flexible strand and a shuttling device passing through a splice region in the flexible strand, the flexible strand having a distal end secured to the fixation device and a proximal end extending from the proximal end of the fixation device, the shuttling device having first and second proximal ends extending from the proximal end of the fixation device;
passing the proximal end of the flexible strand around soft tissue;
capturing the proximal end of the flexible strand with the first proximal end of the shuttling device by passing the proximal end of the flexible strand through an eyelet on the first proximal end of the shuttling device;
pulling the second proximal end of the shuttling device such that the first proximal end of the shuttling device with the captured proximal end of the flexible strand passes through the splice region in the flexible strand to form an adjustable knotless closed loop; and
reducing the perimeter of the knotless closed loop to draw the soft tissue toward the bone to a desired location and with a desired tension.

16. The method of claim 15, wherein the flexible construct is attached to the fixation device by passing the distal end of the flexible strand through the cannulated body of the fixation device and through a hole at the distal end of the fixation device, and tying a static knot in the distal end of the flexible strand on the outside of the distal end of the fixation device to secure the flexible strand to the fixation device.

17. The method of claim 15, wherein the adjustable knotless closed loop is disposed within the cannulated body of the fixation device.

18. The method of claim 15, wherein the adjustable knotless closed loop is formed outside the cannulated body of the fixation device.

19. The method of claim 15, wherein the step of installing the fixation device and tensionable construct in bone comprises the steps of:
   pre-loading the flexible construct in the fixation device;
   securing the fixation device to a driver by tying the flexible strand to the driver; and
   inserting the fixation device into a hole in the bone.

20. The method of claim 19, further comprising the step of releasing the fixation device from the driver and removing the driver.

21. The method of claim 15, wherein the shuttling device comprises a nitinol wire which passes around a post within the fixation device.

22. The method of claim 15, wherein the fixation device comprises a push-in anchor with ribs.

23. The method of claim 15, wherein the fixation device comprises a threaded anchor which is turned into the bone.

24. A method of tissue repair, comprising the steps of:
   installing a fixation device and a flexible construct in bone, the fixation device comprising a cannulated body, a longitudinal axis, a proximal end, and a distal end, the flexible construct being attached to the fixation device and comprising a flexible strand and a shuttling device passing through a splice region in the flexible strand, the flexible strand having a distal end secured to the fixation device and a proximal end extending from the proximal end of the fixation device, the shuttling device having first and second proximal ends extending from the proximal end of the fixation device;
   passing the proximal end of the flexible strand around soft tissue;
   capturing the proximal end of the flexible strand with the first proximal end of the shuttling device;
   pulling the second proximal end of the shuttling device such that the first proximal end of the shuttling device with the captured proximal end of the flexible strand passes through the splice region in the flexible strand to form an adjustable knotless closed loop; and
   reducing the perimeter of the knotless closed loop to draw the soft tissue toward the bone to a desired location and with a desired tension,
   wherein the shuttling device comprises a nitinol wire which passes around a post within the fixation device.

* * * * *